United States Patent [19]
Pappas et al.

[11] Patent Number: 5,133,764
[45] Date of Patent: Jul. 28, 1992

[54] MULTI-COMPONENT PROSTHESIS WITH INCREASED WALL FLEXIBILITY AND SEGMENTED LOCKING RIDGE TO FACILITATE COMPONENT ASSEMBLY

[76] Inventors: Michael J. Pappas, 61 Gould Pl., Caldwell, N.J. 07006; Frederick F. Buechel, 76 Crest Dr., South Orange, N.J. 07079

[21] Appl. No.: 205,315

[22] Filed: Jun. 10, 1988

Related U.S. Application Data

[63] Continuation-in-part of Ser. No. 492,133, May 6, 1983, abandoned.

[51] Int. Cl.⁵ .............................................. A61F 2/34
[52] U.S. Cl. ...................................................... 623/23
[58] Field of Search ...................... 623/16, 18, 19, 20, 623/22, 23

[56] References Cited

U.S. PATENT DOCUMENTS 4,172,296 10/1979 D'Errico ................................ 623/22

FOREIGN PATENT DOCUMENTS 0024442 3/1981 European Pat. Off. ............. 623/22
2592787 7/1987 France ................................... 623/22

Primary Examiner—David Isabella
Attorney, Agent, or Firm—Anthony J. Casella; Gerald E. Hespos

[57] ABSTRACT

A multi-component hip joint prosthesis is provided comprising an acetabular cup and a plastic bearing liner, each of which defines a segmented open shell with an inferior segment thereof removed to provide enhanced flexibility. The enhanced flexibility substantially facilitates the assembly and disassembly of the components. The liner and the cup are retained in their assembled condition by interengagement between a plurality of ridges and at least one groove on the respective components. The plurality of independent ridges enhances the flexibility of the ridges, thereby further mimimizing the assembly forces required. Interengageable keys and keyways on the respective components may be provided to prevent relative rotation therebetween. The cup may comprise a removable tab to facilitate the insertion of a tool between the cup and the liner for prying the liner from the cup if necessary.

17 Claims, 12 Drawing Sheets

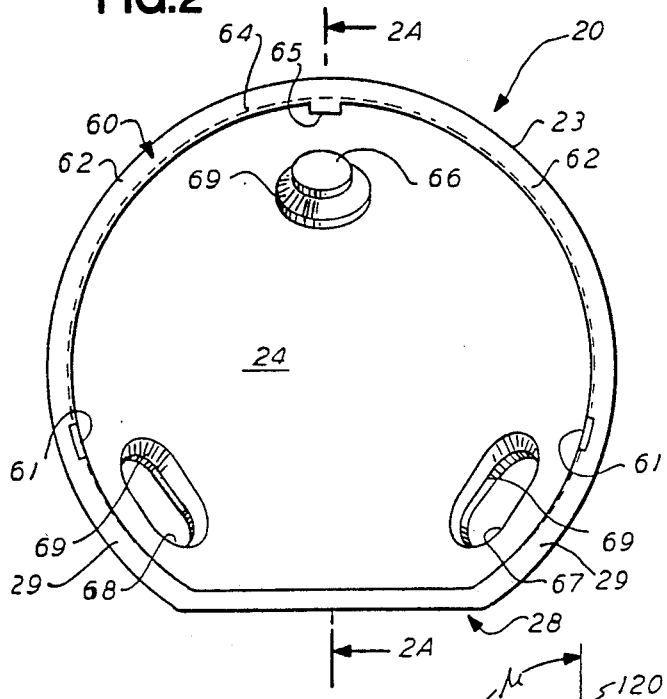
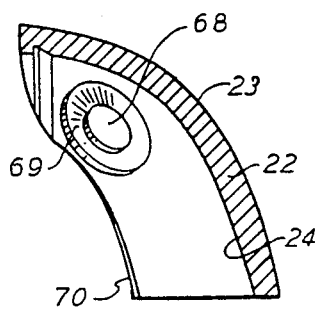
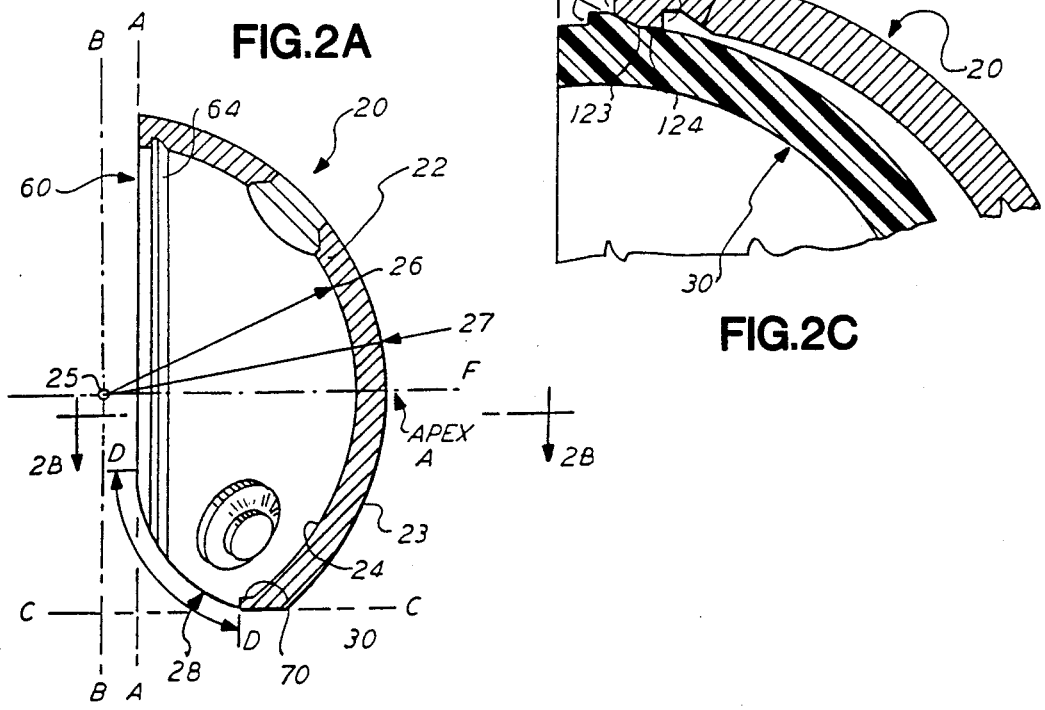
FIG.2
FIG.2A
FIG.2B
FIG.2C

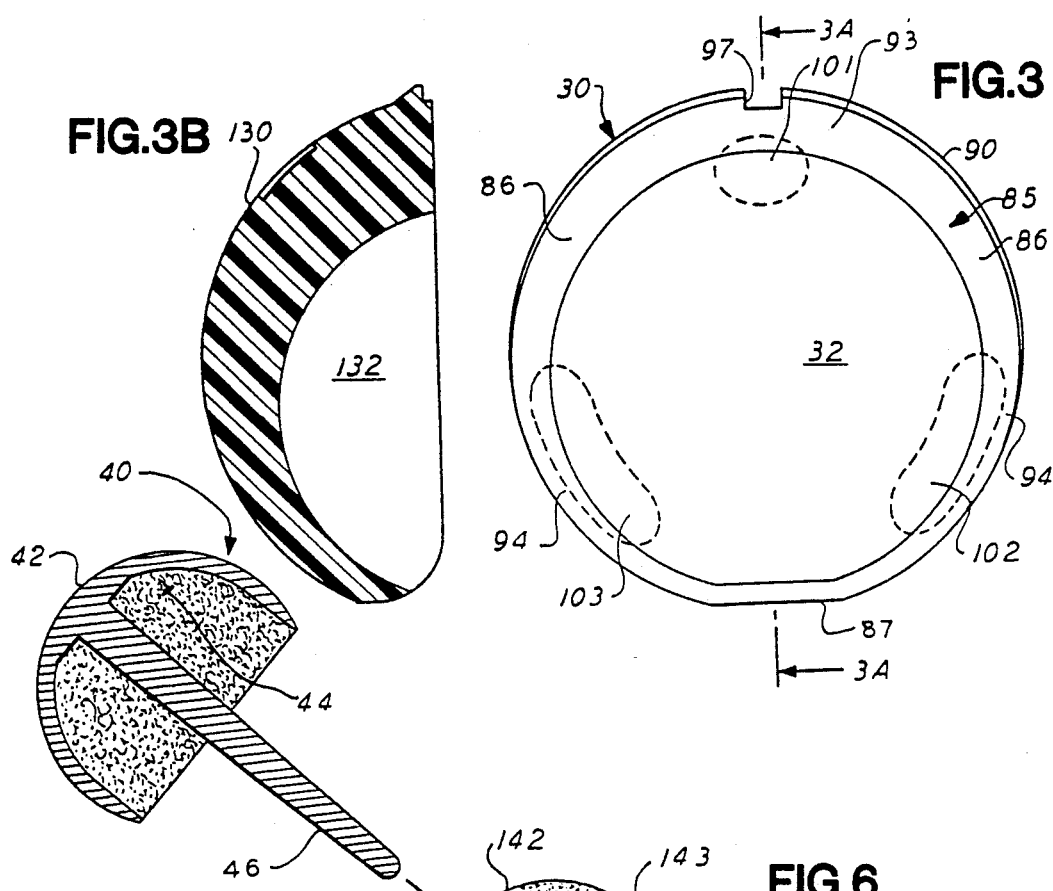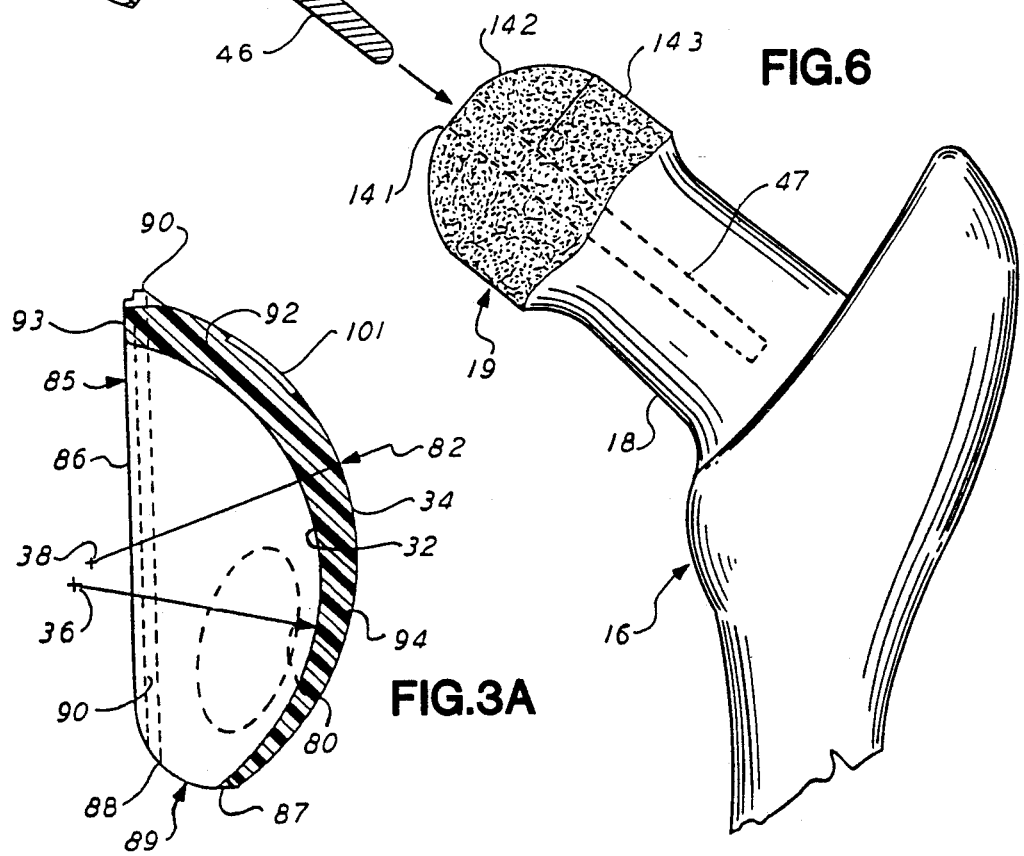

FIG.4
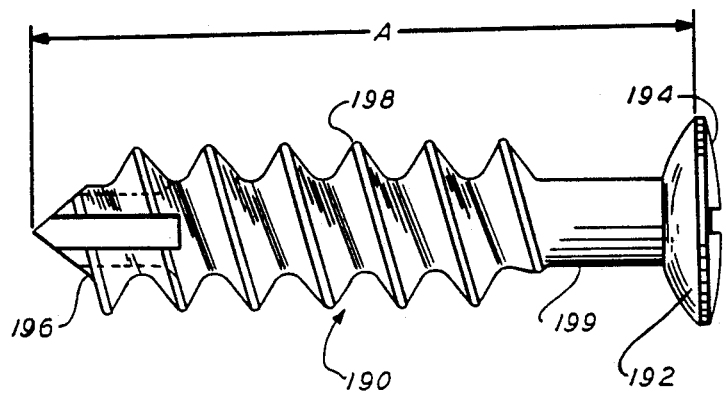
FIG.4A
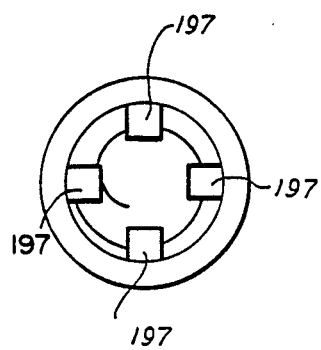
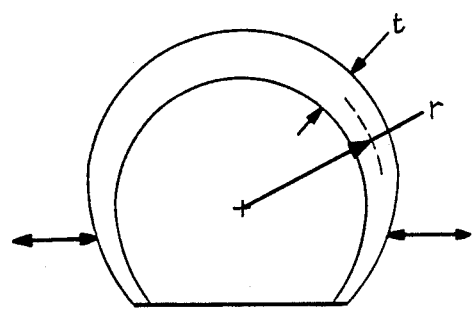
FIG.7B
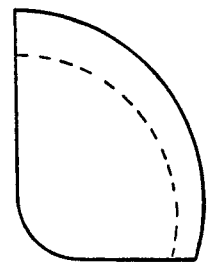
FIG.7A
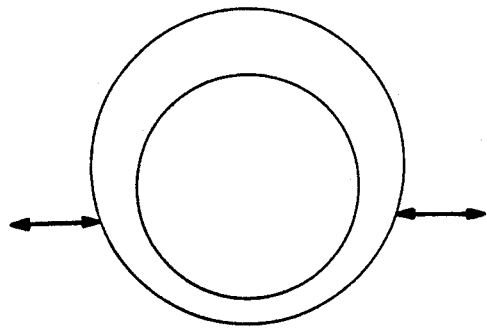
FIG.7D
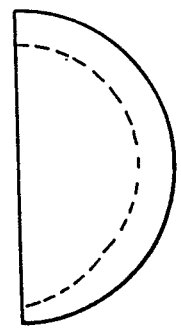
FIG.7C

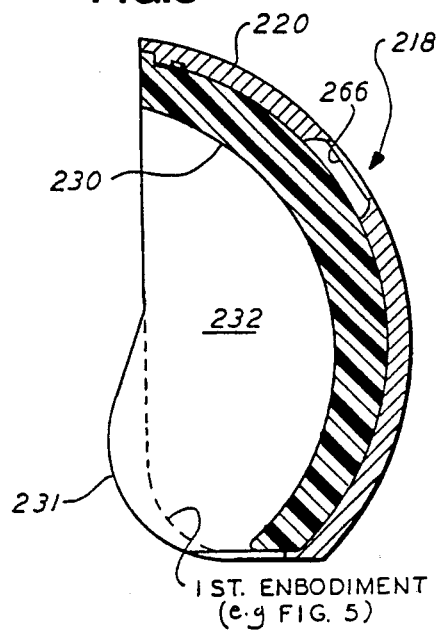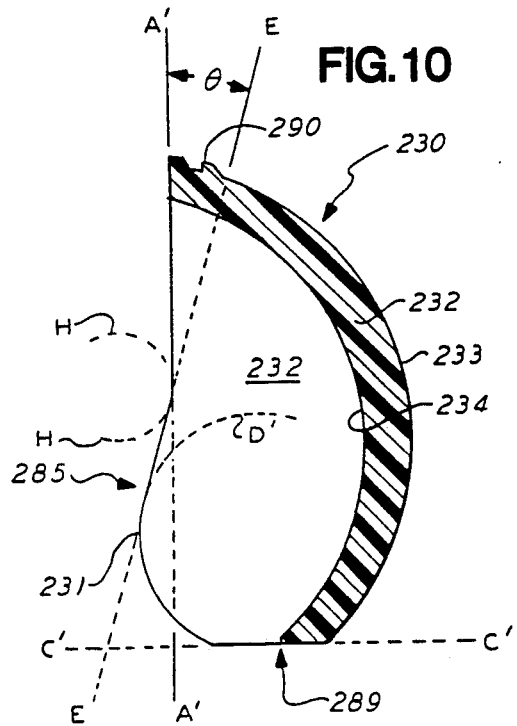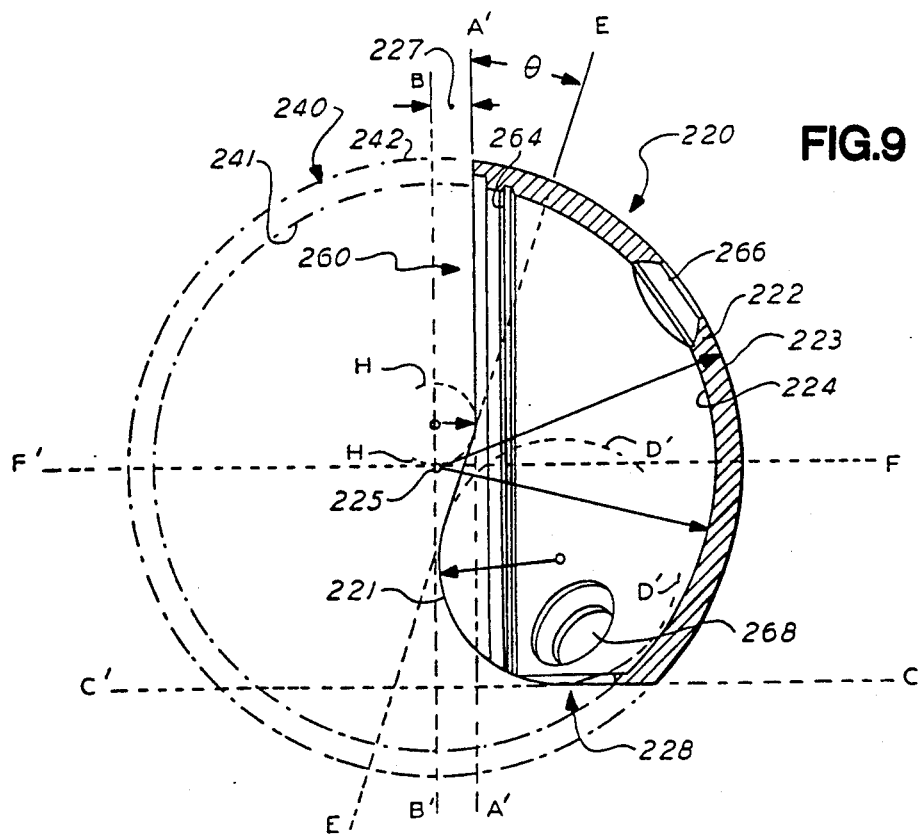

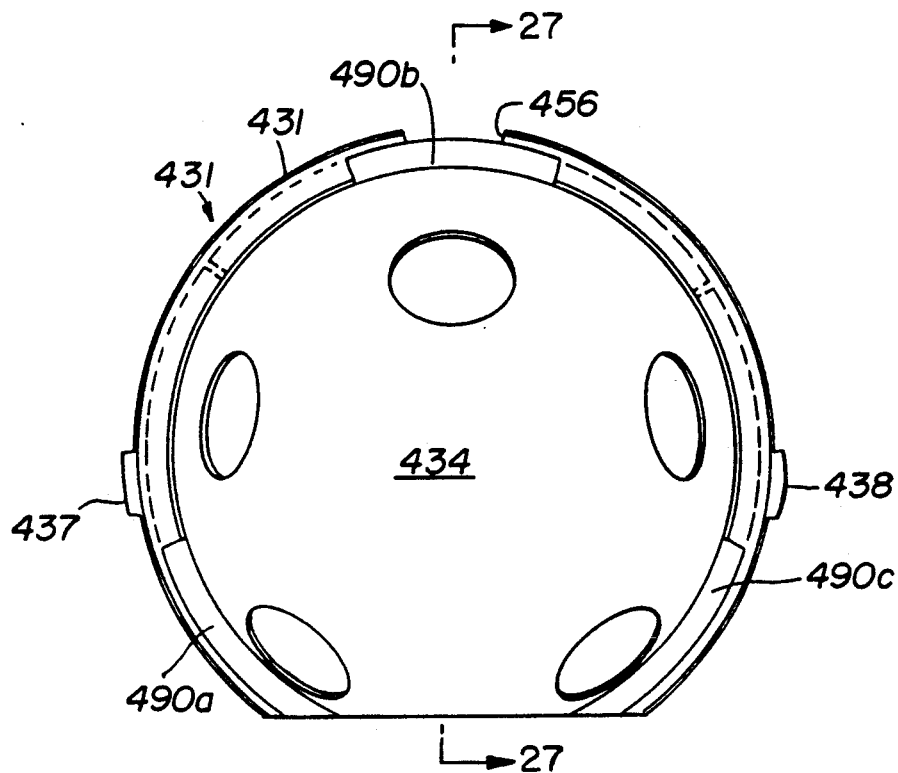
FIG.25
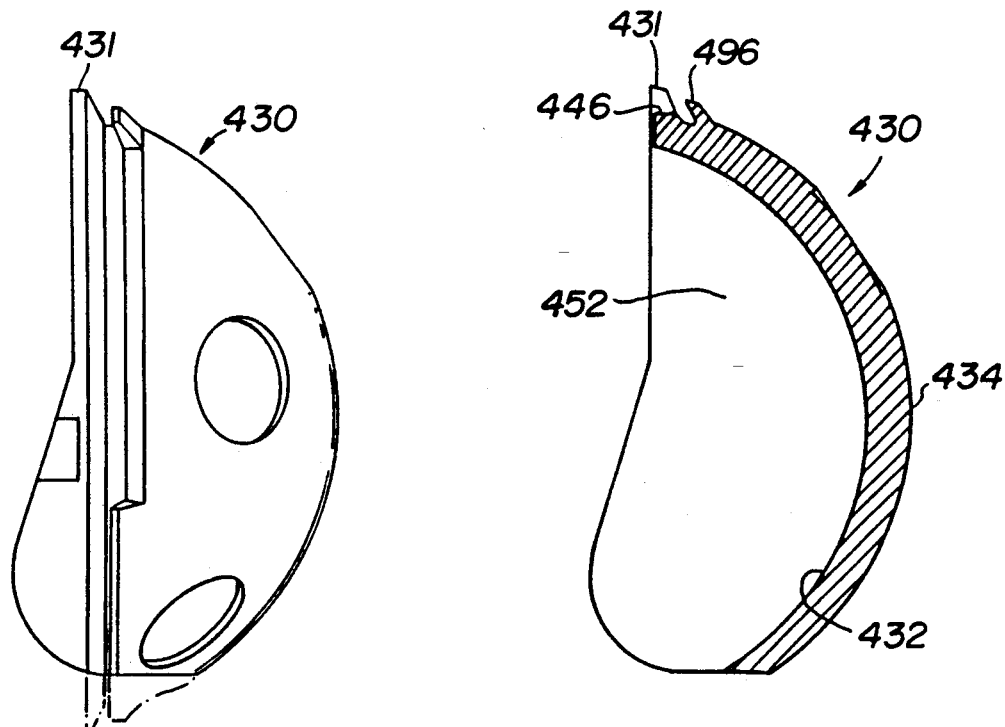
FIG.26
FIG.27

MULTI-COMPONENT PROSTHESIS WITH INCREASED WALL FLEXIBILITY AND SEGMENTED LOCKING RIDGE TO FACILITATE COMPONENT ASSEMBLY

CROSS REFERENCE TO RELATED APPLICATION

This application is a continuation-in-part of U.S. patent application Ser. No. 492,133, filed May 6, 1983, now abandoned entitled "MULTI-COMPONENT PROSTHESIS WITH INCREASED WALL FLEXIBILITY FACILITATING COMPONENT ASSEMBLY", Michael J. Pappas and Frederick F. Beuchel, inventors.

BACKGROUND OF THE INVENTION

This invention relates generally to a new and improved joint prosthesis, and more particularly relates to an improved multi-component joint prosthesis, such as for example a multi-component hip joint prosthesis, wherein at least one of the components may be an open shell.

The conventional prior art total hip prosthesis typically includes a metal femoral head fixtured to the femur and a plastic, generally ultra-high molecular weight (UHMWPe), cup fixtured by cement to the acetabulum such as the type disclosed in U.S. Pat. No. 4,123,806 issued Nov. 7, 1978 to Amstutz et al. The prior art also discloses the use of hip prostheses including metal backed acetabular components in which the acetabular component consists of a metal cup with a plastic bearing insert; examples of such prostheses are given in U.S. Pat. No. 3,840,904 issued Oct. 15, 1979 to Tronzo and U.S. Pat. No. 3,903,549 issued Sep. 9, 1975 to Deyerle. Metal backed acetabular hip prosthesis components have several advantages. The metal or rigid outer acetabular cup produces a much more uniform stress distribution at the interface between the cup and the acetabulum with lower peak forces or stress thereby improving the possibility of long term fixation. Rigidity of the metal outer acetabular cup also reduces distortion of the plastic liner improving its sphericity and therefore contact with the metal femoral head of the hip prosthesis, thereby improving conditions for wear resistance. Further, the use of a separate bearing insert allows replacement of the insert if the insert is damaged intraoperatively, or if the insert becomes excessively worn as a result of long term use, or if as a result of some problem revision is necessary which involves a change in the insert bearing. For example, in the event of revision from a surface replacement type hip prosthesis, which has a fairly large diameter head, to a stem type femoral prosthesis, which includes usually a smaller diameter head, one may simply remove the bearing liner leaving the metal acetabular cup affixed to bone, and replace the liner with another liner or insert of appropriate size for the revised unit. Such revision can, therefore, be made without disturbing the acetabular fixation thereby preventing damage to the acetabular bone.

There is, however, a potential disadvantage associated with the use of a rigid or metal acetabular cup. In the event that a load is applied near the rim of the acetabular cup, the elastic properties of the underlying bone combined with the rigidity of the cup can produce a situation in which the opposite rim tends to be lifted off of its bony bed. This tends to produce tensile loads on the cup and such tensile loads are undesirable in maintaining long term fixation.

In the prosthesis disclosed in the Tronzo patent, an interlock 26 and interlocking groove 28 as described in FIGS. 2–8 of Tronzo are used to prevent rotation of the liner relative to the cup. This connection, however, is not resistant to a tensile withdrawal of the cup from the liner. Such withdrawal can occur as a result of traction forces due to a layer of liquid interposed between the femoral component and the plastic liner coupled with distraction of the femur from the acetabulum during normal activity. Such a situation can produce withdrawal of the plastic bearing from the acetabular cup producing dislocation of the prosthetic component.

The prosthesis described in the Deyerle patent uses an arcuate ridge 32 which engages an arcuate slot 44 as shown in FIGS. 1, 5 and 6 of Deyerle to restrict relative rotation. The Deyerle device uses screws by making use of an annular liner (not identified by number) in conjunction with a retaining screw 30 to trap the liner in the cup. This design, however, experiences difficulty in liner removal because removal of the liner requires removal of the screws from the bone which may produce damage to the bone. Further, the use of such a connection resistance against tensile loading requires the use of screws and many surgeons would prefer in some applications not to use screws for fixation.

Both the Tronzo and Deyerle prostheses use screws. Neither, however, provides the ability of the screws to change their angular orientation significantly to facilitate fixation. Further, neither provides screws near the inferior rim to minimize the possible lifting of the inferior rim as a result of loads applied near the superior rim. Such loads are normal in walking and may exceed eight times body weight in stair climbing and descent. Since the angular orientation of the screw is not adjustable in Tronzo and Deyerle devices, these screw configurations cannot take maximum advantage of possible superior bone stock for screw implantation. Further, Deyerle and Tronzo prostheses both make use of either screws or spikes for fixation. However, when such acetabular components are used with cement, such spikes or screws may not be necessary for fixation and their use makes the operative procedure more difficult and introduces additional damage to the bone.

U.S. Pat. No. 3,608,096 to Link discloses a prosthesis which uses a relieved face on the acetabular shell where a segment of the shell is removed by means of an oblique cut (not identified by number) as described in Column 2, lines 69–72 and Column 3, lines 1–3 to provide a better approximation to the shape of the natural acetabulum so as to increase clearance reducing possible impingement with the femur during certain kinds of activity as described in Column 3, lines 26–29. Further, the outside section 3 as shown in FIG. 1 of the Link patent is eccentric to the cavity 2 although the nature and reason for this eccentricity are not described by Link. Although this oblique and simple relief provides improvement in fit and clearance, still better fit and clearance can be provided by a somewhat more complex relief of the inferior face of the acetabular component.

In view of the above, it is an object of the subject invention to provide a multi-component prosthesis that facilitates assembly and disassembly of the components.

A further object of the subject invention is to provide a multi-component prosthesis that enables the components to be securely retained in their assembled condition and also achieves easy assembly and disassembly for all dimensional ranges of the components dictated by manufacturing tolerances and environmental conditions.

Another object of the subject invention is to provide multi-component prostheses that provide a smaller range of insertion forces for any given range of manufacturing and other size variations.

SUMMARY OF THE INVENTION

The subject invention is directed to a multi-component prosthesis that is easy to assembly and/or disassemble and that is substantially insensitive to dimensional variations in one or more components.

The prosthesis may comprise a first component having a plurality of independently deflectable resilient ridges which are selectively engageable with a second component of the prosthesis. The ability of the flexible ridges to deflect independently substantially reduces assembly forces as compared to prostheses with a single integral ridge extending over a comparable distance.

Assembly of the components of a multi-component prosthesis also may be facilitated by constructing at least one of the components as a non-symmetrical segmented open shell, whereby the segmenting of the shell increases the flexibility of the shell wall, which flexibility in turn facilitates component assembly. Such flexibility also enhances the engagement of retaining means for retaining components together upon assembly. Thus, the above described segmented resilient ridges and the non-symmetrical segmented open shell construction both rely on increased flexibility to achieve the previously stated objective.

Screws utilized to secure a prosthesis component to a bone may be recessed within the seat of a screw hole formed in the component for receiving the screw. A preferred area contact is achieved between the underside of the screw head and the seat of the screw hole by making both the underside of the screw head and the screw hole seat spherical. Additionally, a second component engaging the first component may be provided with a recess overlying the screw hole. Thus, in the event the screw head extends upwardly out of the screw seat the recess accommodates the screw head.

As used in the context of the present invention, and as used in the specification and appended claims, the term "open shell" defines a shell segment produced by cutting a closed shell (i.e. a shell without openings) with a single cutting plane or planar cutting surface cutting through both the exterior and interior surfaces of the shell. The term "segmented open shell" defines a shell segment produced either by cutting an open shell by additional cutting surfaces, or by cutting a closed shell by: a non-planar cutting surface, (e.g. a cylindrical cutting surface); more than one cutting plane; or more than one planar cutting surface. The generation of slots is not considered segmentation in the context of the present invention, since the generation of a slot is the equivalent of splitting the shell rather than removal of a shell segment. Although slotting normally involves removal of a thin segment, such removal is incidental to function.

The prosthesis comprises a cup which is engageable with the bone and a bearing liner which is snapped into engagement with the cup. The inner surface of the bearing liner defines a generally spherical articulation surface which engages the head corresponding prosthetic component. The cup and the bearing liner are both segmented open shells as defined above.

The snapped engagement between the cup and the bearing liner may be defined by a groove on the inner surface of the cup and a plurality of separately deflectable ridges on the bearing liner. The provision of separately deflectable ridges substantially facilitates the intraoperative assembly of the prosthetic device, but still provides a secure engagement of the bearing liner in the cup. The dimensions of the components may be selected such that the ridges are in a deflected condition when the components are assembled to achieve a desirably secure interengagement.

BRIEF DESCRIPTION OF THE DRAWINGS

FIG. 2 is a front elevational view of a metal acetabular cup of the present invention, FIG. 2A is a cross-sectional view taken in FIG. 2 along the line 2A—2A and in the direction of the arrows, FIG. 2B is a cross-sectional view taken along the line 2B—2B in FIG. 2A and in the direction of the arrows, and FIG. 2C is a partial cross-sectional view illustrating the manner of assembly of the acetabular cup and bearing liner retaining means of the present invention.

FIG. 3 is a front elevational view of a bearing liner embodying the present invention; FIG. 3A is a cross-sectional view taken generally along the line 3A—3A in FIG. 3 and in the direction of the arrows, and FIG. 3B is a cross-sectional view of an alternate bearing liner embodiment of the present invention, similar to FIG. 3A but taken in a direction opposite to the arrows 3A—3A in FIG. 3.

FIG. 4 is a side elevational view of a screw of the present invention and FIG. 4A is a left end view of the screw of FIG. 4.

FIG. 6 is a diagrammatical illustration illustrating the assembly of the femoral cap to the resected head of a natural femur.

FIGS. 7A–7D are diagrammatical illustrations of a teaching of the present invention as to increase in flexibility of the wall of a shell to facilitate assembly of prosthesis components.

FIGS. 8–10 are cross-sectional views of a further alternate embodiment of an acetabular cup and plastic bearing liner of the present invention.

FIG. 25 is a rear elevational view showing the exterior of a plastic bearing liner for use with the acetabular cup shown in FIGS. 21-25.

FIG. 26 is a side elevational view of the liner shown in FIG. 25.

FIG. 27 is a cross-sectional view taken along line 27—27 in FIG. 25.

FIG. 31 is a cross-sectional view combining the acetabular cup as shown in FIG. 22 and the plastic bearing liner as shown in FIG. 27.

DETAILED DESCRIPTION OF THE PREFERRED EMBODIMENT

Figure 1:
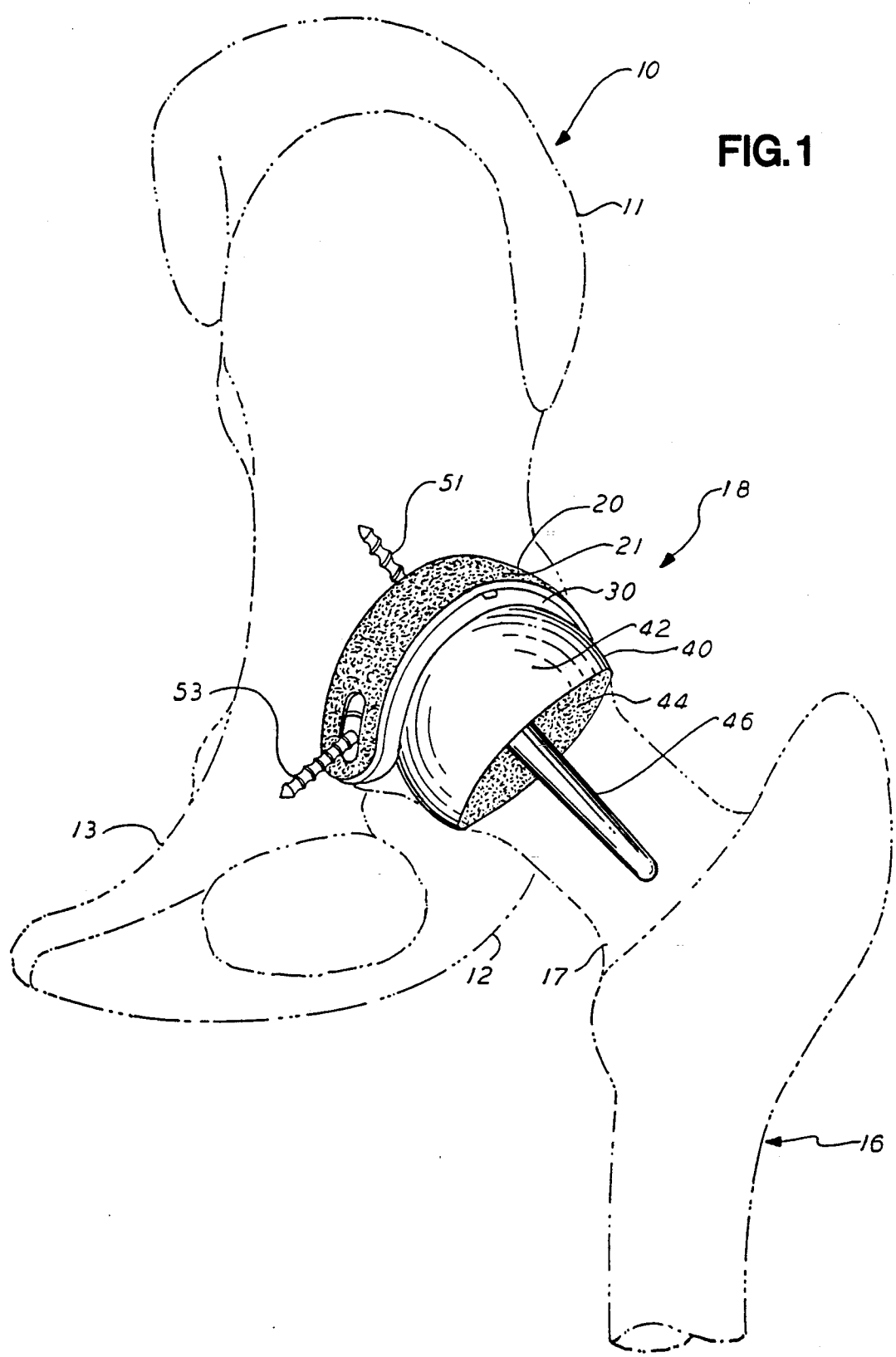
FIG. 1 is a diagrammatical illustration of a surface replacement hip joint prosthesis embodying the present invention and shown diagrammatically as being fixtured by bone ingrowth to the hip bone and femur.

Referring now to FIG. 1, there is shown a diagrammatical illustration of a natural innominate or hip bone 10 including the ilium 11, the ischium 12 and the pubis 13 and a natural femur 16 having a neck 17. Also shown diagrammatically is a hip joint prosthesis embodying the present invention and indicated by general numerical designation 18. The hip joint prosthesis 18 as shown is of the type commonly referred to in the art as a surface replacement hip joint prosthesis. However, it will be understood that the present invention is not limited to the surface replacement type prosthesis, but has wide application to other types of prostheses, such as other types of hip and shoulder prostheses. The prosthesis 18 is shown diagrammatically as being implanted in or fixtured to the hip or pelvic bone 10, or more particularly to the portion of the hip bone providing the acetabulum, or acetabular socket and to the femur 16. The hip joint prosthesis 18 includes a metal acetabular cup 20, a plastic bearing liner or plastic acetabular cup 30 and a metal femoral component or cap 40 of the surface replacement type. However, other femoral prostheses may be employed, such as those commonly referred to as the femoral stem type prostheses.

In the embodiment shown, the metal acetabular cup 20 is provided with a porous outer surface or coating 21 into which the hip bone 10 may grow for permanent fixation. The cup 20 is temporarily fixtured to the hip bone 10 by the use of metal screws 51, 52 (not shown) and 53. The screws 51-53 are used primarily to establish temporary fixation of the acetabular cup 20 to the hip bone 10 during the time required for biological bone or bony ingrowth to occur into the porous coating 21 to provide permanent fixation or to provide augmentation to fixation by use of bone cement. In the preferred embodiment, the metal acetabular cup 20 is temporarily fixtured to the hip bone by the three metal screws, with metal screw 51 being screwed into the ilium 11, metal screw 52 (not shown) being screwed into the ischium 12, and metal screw 53 being screwed into the pubis 13.

The plastic bearing liner 30 is snapped into the metal acetabular cup 20, in a manner described in detail below, and its inner surface provides the acetabular articulation surface.

The metal femoral cap 40 is provided with a highly polished exterior surface 42 providing the femoral articulation surface. The metal femoral cap 40 also comprises a generally hollow interior having an interior porous surface, indicated by general numerical designation 44, into which femur bone may grow to permanently fixture the femoral cap 40 to the resected head 19 of the femur 16 as shown in FIG. 6. Alternatively, the porous surface 44 may be used to improve cement fixation. The femoral cap 40 further comprises a relatively smooth or polished metal stem 46 which is used primarily for alignment purposes and to provide some resistance against fracture of the femoral neck. However, the relatively smooth surface of the metal stem 46 is not a fixation surface. Temporary fixation, during the time required for permanent bone ingrowth fixation to occur, is provided by a press fit between the interior surface 44 and the resected femur head 19 and a press fit between the stem 46 and a hole 47 (FIG. 6) drilled centrally in the resected femur head 19 and femur neck 18. The femoral cap 40 shown in FIG. 1 is the subject of co-pending application Ser. No. 830,208 by the same inventors as the present invention.

Referring now to FIGS. 2, 2A, and 2B, it will be noted that the acetabular cup 20 is a substantially hemispherical cup having a relatively thin wall 22 defined by concentric outer and inner surfaces 23 and 24, respectively, having a common center 25 (FIG. 2A) from which spherical radii 26 and 27 are struck. The acetabular cup 20 is symmetrical about the plane through which section 2A—2A is taken, but is asymmetrical with respect to other planes. In particular, the acetabular cup 20, at its inferior portion indicated by general numerical designation 28, is relieved as may be best seen in FIG. 2A.

One embodiment of the acetabular cup 20 is shown in FIGS. 2-2B. Cup 20 is a multiple segmented shell of revolution, i.e. a segmented open shell, having a generating axis F—F and being of uniform wall thickness and having concentric inner and outer surfaces. The face 60 of the cup 20 is a surface produced by the intersection of a first cutting plane A—A perpendicular to a plane of symmetry of the cup 20, with such plane of symmetry lying in the plane of the drawing. The first cutting plane or planar cutting surface A—A partially defining the face 60 of the cup is closer to a parallel plane B—B through the center of the sphere defining the outer and inner surfaces 23 and 24, respectively, of the cup. The cup 20 is segmented by an inferior surface defined by the intersection of a second cutting plane or planar cutting surface C—C perpendicular to the plane of symmetry and to the first cutting plane A—A defining the face 60 of the cup. The cup 20 has a transition surface 29 (FIG. 2) defined by an intersection of the shell of revolution with a segment D—D of a cylindrical cutting surface perpendicular to the plane of symmetry and tangent to the first and second cutting surfaces or planes A—A and C—C defining the face and inferior surfaces, respectively. Segmentation of the acetabular cup 20 by cutting planes or surfaces A—A, C—C and D—D causes the cup to be a "segmented open shell" as defined above.

A ridge 70 (lower portion of FIG. 2A) protrudes from the interior aspect of the cup adjacent to the inner surface 24. An annular groove 64 cut into the inner surface 24 and lies in a plane parallel to and adjacent the first cutting plane A—A. The cup 20 may be provided at its superior portion, FIG. 2, with a radially inwardly directed key 65 extending inwardly a distance from the face 60 of the cup 20. Additionally, the cup 2 may be provided with a pair of generally opposed slots 61—61 extending inwardly from the face 60 at the lateral or side portions of the cup 20 as shown in FIG. 2. Further, the cup 20 may be provided with three apertures or screw holes 66, 67 and 68 each for receiving a metal screw, such as for example the metal screw 190 of FIG. 4. The apertures may be provided with a recessed spherical seat 69 for accommodating any misalignment with the spherical underside 92 of the screw head 94 of FIG. 4 with the screw head remaining entirely within the recess. Further, to permit the screw inserted through one of the apertures 66–68 to engage the best available bone accessible through the aperture, the spherical seats 69 may be made oblong as shown more clearly with regard to apertures 67 and 68 in FIG. 2.

Referring now to FIGS. 3, 3A and 3B, it will be noted that the plastic bearing liner 30 is a substantially hemispherical cup defined by eccentric inner surface 32 and outer surface 34 and is symmetrical about plane 3A—3A, but asymmetrical in other respects. It will be noted in FIG. 3A that the inner and outer spherical surfaces 32 and 34 have mutually displaced respective spherical centers 36 and 38 with the spherical radius 80 of the inner surface 32 being struck from the spherical center 36 and with the spherical radius 82 of the outer spherical surface 34 being struck from the spherical center 38. The plastic bearing liner 30 is further provided with a face indicated by general numerical designation 85, complementary in shape to the face 60 of the acetabular cup 20. The plastic bearing liner 30 used with the acetabular cup 20 of FIGS. 2-2A is provided with a flat region 86, a curved or cylindrical region 88 and a flat region 87 causing the plastic bearing liner 30 to be relieved at its inferior portion indicated by general numerical designation 89, in the same manner as the metal acetabular cup 20 of FIG. 2A, i.e. by being segmented by cutting planes such as A—A, C—C and D—D of FIG. 2A. The segmentation including the inferior relief causes the plastic bearing liner 30 to be a "segmented open shell" as defined above.

The outer surface 34 of the plastic bearing liner 30, as may be best seen in FIG. 3A, is provided with an interrupted annular ridge 90. More particularly, the annular ridge is interrupted by the relieved inferior portion 89 or by the circular or cylindrical portion 88 of the face 85. The eccentric inner and outer surfaces 32 and 34, respectively, provide the plastic bearing liner 30 with a wall 92, as may be best seen in FIG. 3A, which wall is thicker at its superior portion 93 and which is thinner at its lateral portions 94—94 (FIG. 3) adjacent the inferior portion 89 of the plastic bearing liner 30. This is done to provide a greater thickness of bearing, thereby allowing greater wear in the superior aspect where most wear occurs. This also produces a somewhat thinner sidewall laterally, anteriorly and posteriorly, thereby increasing flexibility of the wall 92 in the region where the wall must be compressed to assemble the plastic bearing liner 30 into the acetabular cup 20. Further, as may be best seen in FIG. 3, the plastic bearing liner 30 may be provided at its superior portion 93 with a radially inwardly extending keyway 97 for receiving the key 65 of the acetabular cup 20, as shown in FIG. 2.

The outer surface 34 of the plastic bearing liner 30 may be provided with a plurality of mutually displaced recesses 101, 102 and 103 for overlying the apertures 66, 67 and 68 of the cup 20, shown in FIG. 2, and their spherical, and oblong spherical, seats 69 which help prevent contact between the plastic bearing liner 30 and the screw head where the screw is not properly seated. The interrupted annular ridge 90 is complementary to and closely matches the interrupted annular ridge 64 of the acetabular cup 20. Similarly, the outer surface 34 of the plastic bearing liner 30 closely matches the spherical inner surface 24 of the acetabular cup 20. The spherical inner surface 32 of the plastic bearing liner 30 provides the acetabular articulation surface.

Figure 5:
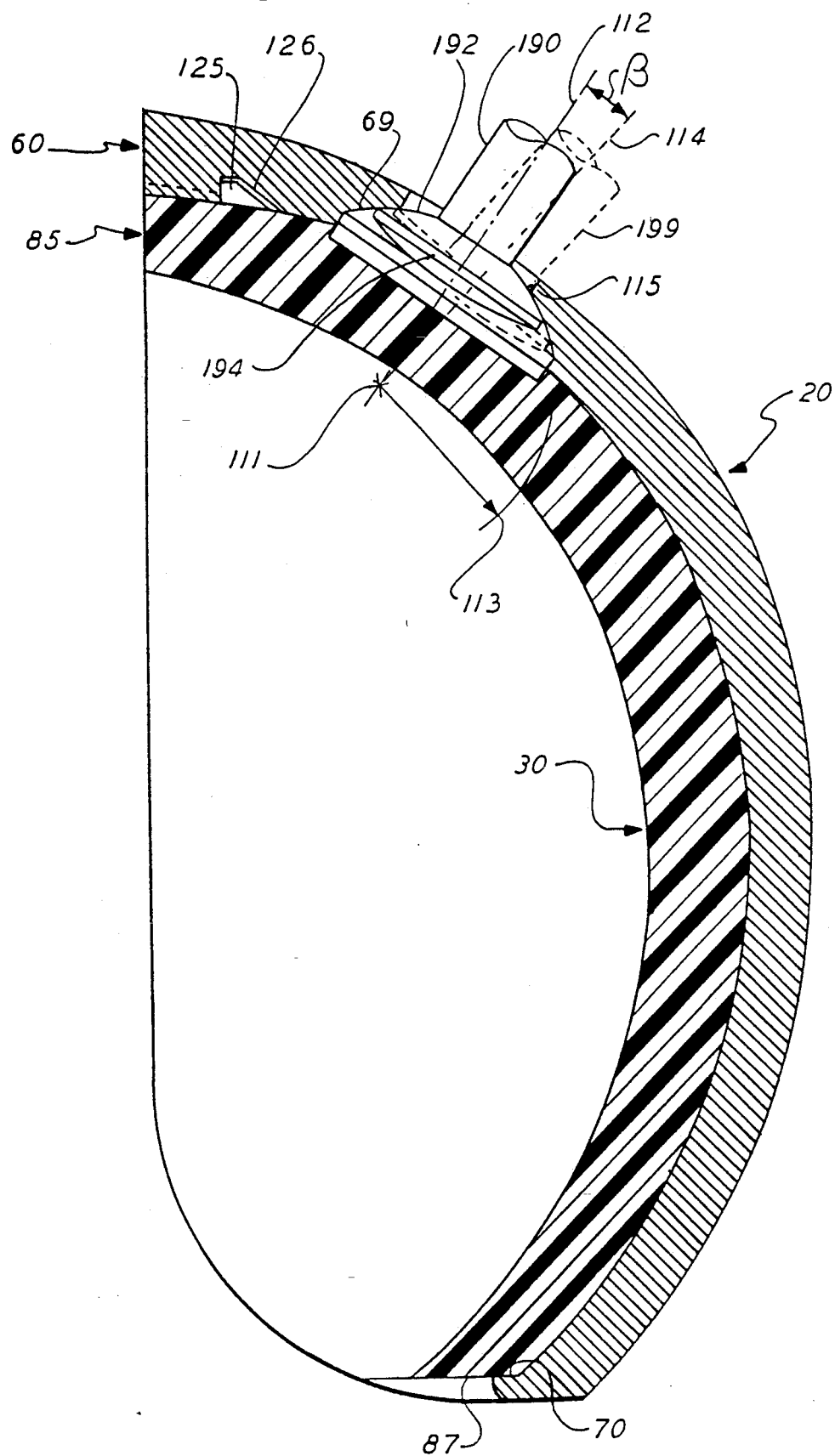
FIG. 5 is an assembly view of the acetabular cup of the present invention and a bearing liner of the present invention, the bearing liner being an alternate embodiment of the liner of FIG. 3, and such illustration showing the assembly as it would look in cross section were such cross-sectional assembly view to be taken along lines such as 2A—2A in FIG. 2 and 3A—3A in FIG. 3.

The inferior flat surface 87 of plastic bearing liner 30 engages the ridge 70 on the acetabular cup 20 restraining, in conjunction with key 65 and keyway 97, axial rotation of plastic bearing liner 30 with respect to acetabular cup 20 about generating axis F—F as shown in FIG. 5.

A cross section of the partially assembled insert and acetabular cup in the region of the interconnecting ridge and groove is shown in FIG. 2C. The ridge and groove faces 125 and 126, respectively, are substantially parallel to the faces 85 and 60 of the insert and cup, respectively. The medial aspect of the ridge is at an angle relative to the face. Upon assembly, using inward forces with substantial force components parallel to the generating axis (F—F of FIG. 2A), the medial aspect of the ridge 90 engages an edge 123 of the interior surface 24 of the acetabular cup. Such engagement produces forces with substantial lateral components generally perpendicular to the generating axis, such components tending to compress the plastic bearing liner 30 or expand the acetabular cup 20. The side walls of the plastic bearing liner 30 or cup 20 are relatively laterally flexible due to the above described segmentation. Therefore, sufficient deformation of the plastic bearing liner 30 and cup 20 is easily produced. This deformation allows the ridge 90 to pass the inside region 124 of the cup 20 adjacent the groove 64, and allows the ridge 90 to engage the groove 64, thereby relieving the compressive and expanding forces and allowing the components to assume the undeformed states.

Removal of the plastic bearing liner 30 from the acetabular cup 20 by use of outward forces with substantial force components parallel to the generating axis (F—F of FIG. 2A) is extremely difficult since the engaging faces 125 and 126 on the liner and cup respectively are perpendicular to the generating axes and thus fail to produce any significant lateral forces compressing the plastic bearing liner 30 or expanding the acetabular cup 20. Rather the forces will be essentially parallel to the generating axis. Therefore, due to the curved shape of the components, these forces will tend to expand the plastic bearing liner 30 and compress the cup 20 thereby locking the components together. Disassembly can be carried out only by use of instruments designed to be inserted into the slots 61—61 (FIG. 2) to apply lateral forces compressing the plastic bearing liner 30 or expanding the cup 20. Due to the nature of the segmentation of these segmented open shell components described, relatively low lateral forces are needed to disassemble the components. Such lateral forces cannot be produced in these components in an implanted prosthesis. Even if such forces could be produced, they would be resisted by the head of the femoral component 40 which prevents contraction of the plastic bearing liner 30 and by the acetabulum. Thus the plastic bearing liner 30 cannot be removed while it is in engagement with the femoral component 40, and dislocation resulting from distraction forces as the result of fluid between the femoral component and the liner cannot occur. For the case of a metal acetabular component 20, which is very stiff compared to plastic, and a plastic bearing liner 30, dislocation of the hip is necessary to remove the plastic bearing liner 30.

The increased flexibility of the segmented open shells described above can be understood by examining FIGS. 7A-D. FIGS. 7A and B illustrate a "segmented open shell" in accordance with the present invention, while FIGS. 7C and D illustrate "open shells" of the prior art type disclosed in U.S. Pat. No. 4,123,806 to Amstutz et al. noted above. It is seen from FIGS. 7A-B that removal of the inferior shell segment removes a major lateral load supporting segment. In shells where the wall thickness t is substantially smaller than the half the radius r of the shell, such segmentation eliminates most of the circumferential compressive stiffness of the wall, thus making bending stiffness dominate. Since for such shells bending stiffness is much less than circumferential stiffness, flexibility of the wall of the "segmented open shell" is greatly increased. Increased flexibility results in a smaller variation in inserting forces for any given range of manufacturing and other size variations while still achieving a tight fit of components within the tolerance range.

With regard to the screw 190, which may be utilized in the present invention, and referring to FIG. 1, it will be noted that in addition to the above-described screw structure the end of the screw 196 may be provided with radially disposed slots, as shown in FIG. 4A, which slots provide self-cutting action so that a cap need not be used in conjunction with the screw. Preferably, the screw is made of a metal alloy the same or similar to that of the metal acetabular cup 20 and it has been found to be preferably to provide several sized screws for different fixation conditions. The threads 198 are preferably large since they are for the purpose of screwing and holding into cancellous bone. Further, it has been found that the screw for fixation into the ischium 12, FIG. 1, is somewhat shorter than the screws used for fixation in the ilium 11 and pubis 13. Of course, the spherical underside 192 of the screw head 194 matches the spherical seats 69 of the apertures 66, 67 and 68 of FIG. 2.

It may be seen from FIG. 5 that the screw 190 can be moved through an angle $\beta$ about center 111 with the spherical underside 192 of screw 190 remaining in full contact with spherical seat 69 as observed by the motion of the screw axis from line 112 to 114 at which point the shank 199 contacts the edge 115 of hole 66 limiting further motion.

Before describing in detail the manner of assembly and disassembly of the metal acetabular cup 20 and the plastic bearing liner 30, and the assembly of the metal femoral cap 40 to the resected femur 16, a brief description of the surgical implantation or fixation technique is presented. The acetabulum, or acetabulum socket or cavity provided by the hip bone 10, FIG. 1, is reamed in an ordinary fashion as would be done for the implantation of any acetabular hip cup, such being well known to those skilled in the art, particularly orthopaedic surgeons skilled in the art. A trial component is then used to orient the acetabular cup to the acetabulum and is used to mark out the location of the holes to be drilled for accepting the screws 190. The metal acetabular cup 20 is provided with a slightly larger spherical outer surface 23 than the prepared acetabular cavity and the acetabular cup is then anatomically aligned and pressed into place. The holes are then drilled into the acetabulum through the apertures 66, 67 and 68, and screws 51, 52 and 53 of FIG. 1, which screws may be the screw 190 of FIG. 4, are then screwed into the hip bone providing the acetabular cavity to temporarily fixture the metal acetabular cup 20 to the hip bone. It will be understood that the spherical underside of the screw heads, e.g. spherical underside 192 of FIG. 4, engages the spherical seats 69 of the acetabular cup apertures and since the shank 199 of (FIG. 4) the screw is made to be much smaller than the diameter of the apertures, this allows the head of the screws to be pivoted about a point 111, FIG. 6, so that the screw may be oriented at an angle $\beta$ relative to the axis 112 of the aperture as shown in FIG. 5. Thus, it will be understood, positioning variation is provided by the present invention, and this positioning configuration has been found to be important in seeking out the best available bone for the screw to engage. Further, this positioning variation is accomplished while maintaining excellent contact between the screw head and its spherical seats. The oblong spherical seats of the apertures, FIG. 2, allow for similar misalignment but also allow for a further change in the location of the screw within the confines of the seat thereby again enhancing effective utilization of existing bone stock and permitting a greater change in location of the screw within the aperture to permit the screw to engage the best available bone accessible through the aperture.

The plastic bearing liner 30 is now "snap-fitted" into place in the fixtured metal acetabular cup 20 in accordance with the teachings of the present invention. Spherically radially inwardly directed forces, such as may be generated digitally and quite easily by the fingers of the operating surgeon, are applied to the thinner wall regions 94—94 of the plastic bearing liner 30 to flex the lateral thinner wall portions inwardly. This permits the interrupted annular ridge 90 of the plastic bearing liner 30 to be inserted into and engage the interrupted annular groove 64 of the metal acetabular cup 20. Thus, the inwardly flexed plastic bearing liner 30, in combination with the respective relieved inferior portions 28 and 89 of the acetabular cup 20 and plastic bearing liner 30, readily permit the flexed plastic bearing liner 30 to be inserted or "snap-fitted" into the metal acetabular cup 20. The key 65 of the acetabular cup 20 will be aligned with and received in the key-way 97 at the superior portion of the plastic bearing liner 30. Additionally, the flat end portion of the wall 92 of the plastic bearing liner 30 will be aligned with and engaged by the flat projection or ridge projecting inwardly at the inferior portion 28 of the metal acetabular cup 20. The key and key-way, and engaged flat surfaces, resist relative rotation between the plastic bearing liner 30 and the metal acetabular cup 20 upon torsional loads applied thereto during articulation of the hip joint. Further, it will be understood, as may be better seen in FIG. 5, the respective faces 60 and 85 of the acetabular cup 20 and plastic bearing liner 30 align, transversely, and present a common face for the assembled cup 20 and plastic bearing liner 30 and with the common relieved inferior portions thereof permitting a greater range of articulation of the femur bone without impingement with the plastic bearing liner 30 and cup 20, thereby further reducing the possibility of impingement of the cup 20 and plastic bearing liner 30 by the femur during joint articulation.

With the acetabular cup 20 and plastic bearing liner 30 now firmly in place in the acetabulum, the head of the femur 16 is resected or prepared by suitable instruments to provide a resected head, as shown in FIG. 6, complementary to the interior surface 44 of the metal femoral cup 40. More particularly, the resected head 19 of the femur 16 is prepared to provide the resected head with a flat portion 141 continuing into a spherical portion 142 continuing into a cylindrical portion 143. It will be understood that the outer dimensions of the resected femur head 19 are made somewhat larger than the inner dimensions of the inner surface 44 of the metal femoral cap 40 and the centrally drilled hole provided in the resected femur head 19 and femur neck 18 is made somewhat smaller in diameter than the diameter of the femoral cap stem 46. Thus, the femoral cap 40 may be press fitted onto the femure head 19 with such press fitting providing temporary fixation of the femoral cap 40 to the femur head 19. The hip joint is then reduced with the outer spherical surface 42 of the metal femoral cap 40 being received within the spherical inner surface 32 of the plastic bearing liner 30 for joint articulation. The articulation between the polished outer spherical surface 42 of the metal femoral head 40 and the spherical inner surface 32 of the plastic bearing liner 30 provide low friction, long wearing articulation and, the relatively larger articulation surfaces associated with the surface replacement prosthesis provide greater potential for extended wear resistance than do the smaller articulating surfaces associated with the conventional total hip prosthesis known to the prior art.

It will be further understood in accordance with the teachings of the present invention that the screws described above, providing temporary fixation of the metal acetabular cup to the hip bone providing the acetabulum provide temporary fixation during the period of time required for hip bone ingrowth and to the porous outer surfaces 23 of the acetabular cup 20 which bone ingrowth provides the permanent fixation of the metal acetabular cup 20 to the hip bone 10. Similarly, the press fit between the metal femoral cap 40 and the resected femur head 19 provides temporary fixation of the metal femoral cap 40 to the femur during the time required for femur bone ingrowth at the resected head 19 to grow into the porous inner surface 44 of the femoral cap 40 to permanently fixture the femoral cap 40 to the resected femur head 19. It has been found that such respective temporary fixations are sufficient to maintain the respective components fixtured during normal joint articulation and during the time required for bone ingrowth and biological permanent fixation.

In accordance with the further teachings of the present invention, the plastic bearing liner 30 may be readily and easily removed from the metal acetabular cup 20. Referring to FIG. 2, and as noted above, the lateral portions of the metal acetabular cup 20 are provided with generally opposed slots 66 into which a tool may be inserted and operated readily by digital force supplied by the operating surgeon to again flex the inner lateral regions of the plastic bearing liner walls 94—94 inwardly to flex the plastic bearing liner inwardly to permit the interrupted annular ridge 90 to be disengaged from the interrupted annular groove 64 and such engagement, in combination with the respective relieved inferior portions 28 and 89 of the cap and liner, permit the inwardly flexed plastic bearing liner 30 to be readily removed from the metal acetabular cup 20. It will be understood that in accordance with the further teachings of the present invention, the slots 61—61 could be provided on the outer surfaces of the plastic bearing liner 30, at the same positions, or mating opposed slots could be provided in both the metal acetabular cup and the plastic bearing liner.

Referring again to the recesses 101, 102 and 103, provided in the outer spherical surface 34 of the plastic bearing liner cup 30, FIG. 3, it will be understood that these recesses overlie the screw heads of the screws 51, 52 and 53 temporarily fixturing the metal acetabular cup 20 to the hip bone 10, and it will be understood that these recesses accommodate these screw heads even during any misalignment or relocation of the screws within the apertures as described above. Further, and in accordance with the teachings of the present invention, the plastic bearing liner portions providing the recesses engage the metal screw heads and prevent them from becoming unscrewed during joint articulation.

Referring again to FIG. 3B, it will be noted that the alternate plastic bearing liner shown herein, with a smaller inside diameter than the plastic bearing liner of FIG. 3A, may be used in the event that the conventional metal femoral stem is used in the femur instead of the metal femoral cap 40 of the present invention, the spherical inner surface 132 of the plastic bearing liner alternate embodiment 130 of FIG. 3B being dimensioned to closely match the exterior surface of such metal femoral stem.

Still further in accordance with the teachings of the present invention, the bearing liner, instead of being plastic as described above, may be ceramic and in such alternate embodiment it will be understood that the relatively thin walls of the metal acetabular cup 20 will be flexed outwardly to permit the ceramic bearing liner to be inserted into and removed from the metal acetabular cup 20; it will be understood that the ceramic bearing liner is brittle and less flexible than the metal acetabular cup but will still undergo some slight inward flexing but due to the relieved inferior portions only a very slight outward flexing of the metal acetabular cup or very slight inward flexing of the ceramic liner, in combination with the relieved inferior portions, will readily permit the insertion and removal of a ceramic bearing liner from the metal acetabular cup.

An important advantage of a replaceable bearing liner is that a surface replacement type hip may be revised to a conventional total hip using a femoral stem without disturbing acetabular fixation by removing the plastic bearing liner shown as embodiment 30 intended for use with a surface replacement femoral component and replacing it with the plastic bearing liner embodiment 130 intended for use with a femoral stem prosthesis.

Referring again to FIGS. 7A-D where it is shown that by open shell segmentation the flexibility of the side walls may be increased, it should be observed that this increase in flexibility will result in an increase in the amount of allowable engagement between the groove 64 (FIG. 2A) and the ridge 90 (FIG. 3A) for a given assembly load compared to a non-segmented open shell since the segmented open shell is more easily compressed. Thus, the strength of this engagement can be increased and/or manufacturing tolerances associated with this engagement can be less critical than those associated with a non-segmented open shell.

Referring now to FIGS. 8-10, there is illustrated a further alternate embodiment of the present invention also embodied as a multi-component hip joint prosthesis indicated by general numerical designation 218 and including a generally semi-hemispherical outer metal acetabular cup 220 and a generally semi-hemispherical inner plastic bearing liner 230. The cup and liner are illustrated in their assembled position in FIG. 8 and shown, respectively, in cross section in FIGS. 9 and 10 with FIGS. 9 and 10 being similar to the cross-sectional views of FIGS. 2A and 3A, respectively, and it will be understood that the front views of the cup and liner 220 and 230 merely would be similar to the front views shown in FIGS. 2 and 3, respectively, and hence are not shown.

Acetabular cup 220 and plastic bearing liner 230 are structurally similar to the earlier described acetabular cup 20 and plastic bearing liner 30, that is the metal acetabular cup 220 and the plastic bearing liner 230 are each a "segmented open shell" as defined hereinabove with each having an inferior segment removed which increases the flexibility of the cup and liner wall thereby facilitating their assembly and disassembly by reducing the assembly and disassembly forces required. It will be recalled with regard to the "segmented open shell" of the present invention illustrated in FIGS. 7A and 7B and as taught in the associated specification hereinabove, that were a major load supporting inferior segment resisting assembly forces not removed, but present as shown in the case of the prior art "open shells" illustrated in FIGS. 7C and 7D, such inferior segment if present would resist the assembly (also disassembly) forces and would, as taught above, make the cup and liner more stiff in compression thereby requiring the application of greater assembly and disassembly forces to produce assembly and disassembly. In addition, we also taught above, this is particularly advantageous with regard to intra-operative assembly of the prosthesis within a surgical cavity.

Primarily, the hip joint prosthesis alternate embodiment 218 of the present invention differs from the earlier described embodiments due to the face that the metal acetabular cup 220 and plastic bearing liner 230 are each provided with a protrusion, i.e. lateral protrusion, at their anterior and posterior wall portions, the posterior protrusions 221 and 231 of the cup 220 and the plastic bearing liner 230, respectively, being shown in the cross-sectional drawings of FIGS. 9 and 10.

Referring now particularly to FIG. 9, the segmenting of the segmented open shell acetabular cup 220 will be described in detail. FIG. 9 is a cross-sectional view, as noted above, and is taken through the plane of symmetry which plane of symmetry, it will be understood, lies in the plane of the drawing. The metal acetabular cup 220 is segmented by a plurality of cutting surfaces. In particular, a first cutting plane or planar cutting surface A'—A' is perpendicular to the noted plane of symmetry. A second cutting plane or planar cutting surface C'—C' is perpendicular to the plane of symmetry and intersects the first planar cutting surface A'—A'. The second planar cutting surface C'—C' removes a major load supporting inferior segment resisting assembly and disassembly forces as in the embodiment of the present invention illustrated diagrammatically in FIGS. 7A and 7B, and relieves the inferior portion 228 of the cup wall 222. A third cutting plane or planar cutting surface E—E is perpendicular to the plane of symmetry and inclined at an angle O with respect to the first cutting surface A'—A'. A first cylindrical cutting surface D'—D' is perpendicular to the plane of symmetry and tangent to the second and third planar cutting surfaces C'—C' and E—E, respectively. Finally, a second cylindrical cutting surface H—H is perpendicular to the plane of symmetry and tangent to the first and third planar cutting surfaces A'—A' and E—E. The first planar cutting plane A'—A' is relieved or displaced medially from the center of curvature 225 as shown by the double headed arrow 227 extending between the cutting surface A'—A' and a parallel plane B'—B' extending through the center of curvature 225. It will be noted from FIG. 9 that such cutting surfaces define the cup face indicated by general numerical designation 260 and that the second through fifth cutting surfaces produce protrusions at the anterior (not shown) and posterior 221 portions of the wall 222 of the segmented open shell or metal acetabular cup 220.

The segmenting of such cutting surfaces may also be understood in the context of the closed shell 240 shown partially and in dashed outline in FIG. 9. The closed shell 240 is a solid of revolution (including the spherical wall 222 of the segmented open shell 220), has a generating axis F'—F' and has spherical inner and outer surfaces 241 and 242 (portions providing the spherical outer and inner surfaces 222 and 224, respectively, of cup 220). It will be noted and further understood that the above-described cutting surfaces, A'—A', etc., segment by passing or cutting through the wall and inner and outer spherical surfaces of the shell as is known by those skilled in the art in the segmenting of any shell.

Referring now to FIG. 10, it will be understood that the plastic bearing liner 230, as noted above, is also a segmented open shell being segmented by cutting surfaces A'—A', C'—C', E—E, D'—D' and H—H, as shown in FIG. 10, and which cutting surfaces are identical, or substantially identical, to the correspondingly identified cutting surfaces of FIG. 9. The cutting surfaces of FIG. 10 also define the face, indicated by general numerical designation 285, of the plastic bearing liner 230, and hence it will be understood that the faces 260 and 285 of the cup 220 and the plastic bearing liner 230, respectively, are complementary as may be noted from the assembly view of FIG. 8. As may be understood by reference to FIGS. 9 and 10, generally, the superior portion of the respective faces 260 and 285 is defined by the planar cutting surface A'—A' and the inferior portion of the respective faces is defined by the remaining cutting surfaces. Further, cutting surfaces C'—C', D'—D', E—E and H—H also produce protrusions at the anterior (not shown) and posterior 231 portions of the wall 232 of the plastic bearing liner 230. The planar cutting surface C'—C' removes a major load supporting inferior segment resisting assembly and disassembly forces (same as in the embodiment of the present invention illustrated in FIGS. 7A and 7B) and relieves the inferior portion 289 of the liner wall 232 thereby increasing, particularly, the flexibility of the anterior and posterior wall portions. This facilitates the insertion of the plastic bearing liner 230 into the cup 220 for assembly and the removal of the plastic bearing liner 230 from the cup 220 for disassembly. The liner 230 is provided with a spherical outer surface 233 for engaging the spherical inner surface 224 of the cup 220, and with a spherical inner surface 234 for articulating with the outer spherical surface of a spherical head such as the outer surface 42 of the femoral cap 40 of FIG. 1. The outer surface 233 and inner surface 234 may be either concentric or eccentric as shown in FIGS. 3A and 3B and described above.

As may be noted from FIG. 8, the posterior protrusions of the cup 220 and plastic bearing liner 230 of the alternate hip prosthesis embodiment 218 extend laterally beyond the corresponding portions of the cup 20 and liner 30 of the first embodiment indicated in dashed outline in FIG. 8. The significance and further advantages of these protrusions are illustrated in FIGS. 11-13.

Figure 11:
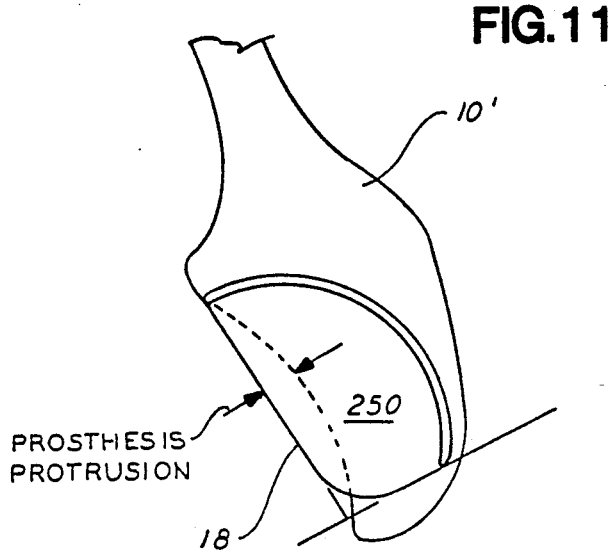
FIG. 11–13 are diagrammatical illustrations showing the advantages of the further alternate embodiment and illustrating the features causing this embodiment to be the preferred embodiment.
Figure 12:
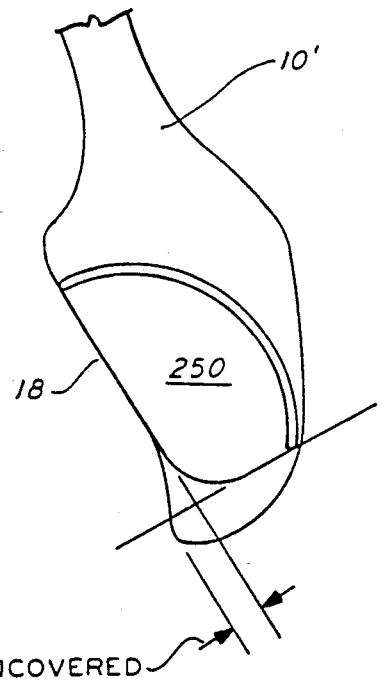
Figure 13:
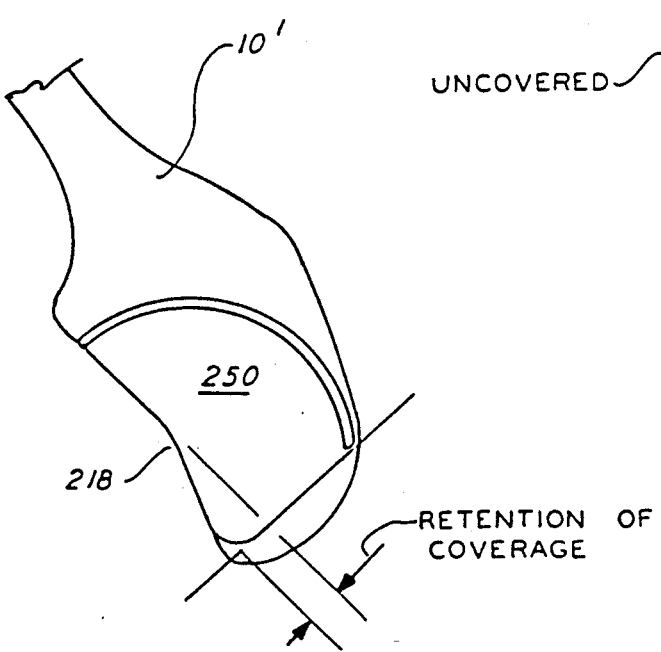

Referring now to FIGS. 11-13, the lateral portion of a natural hip bone 10' having a natural acetabulum or natural acetabular cavity 250 is illustrated in cross section. Were the earlier described hip prosthesis embodiment 18 (FIG. 1) to be dimensioned so as to precisely fit or match the natural acetabular cavity 250, as illustrated in FIG. 11, a portion of the hip prosthesis 18 would protrude laterally beyond the borders of the natural acetabular cavity 250 as illustrated by the opposed arrows shown. Alternatively, were the earlier described hip prosthesis 18 to be dimensioned so as not to protrude laterally beyond the border of the natural acetabular cavity 250, then as shown by the opposed arrows in FIG. 12, this would leave, undesirably, a substantial portion of the inferior aspect of the natural acetabular cavity 250 and its natural acetabular cartilage uncovered. However, as may be noted from FIG. 13, the alternate hip prosthesis embodiment 218 of the present invention eliminates the prosthesis extrusion illustrated in FIG. 11 and at the same time substantially covers the natural acetabular cavity 250 and its natural acetabular cartilage as shown. Accordingly, it will be understood that the alternate hip prosthesis embodiment 218 is the preferred embodiment of the present invention since it has better conformance to the shape of the natural acetabular cavity 250 and allows replacement of most of the surface of the natural acetabular cavity and acetabular cartilage without protrusion of the prosthesis beyond the bony borders of the natural acetabulum. Such protrusion (FIG. 11) is undesirable since such protrusion may produce impingement between the acetabular hip prosthesis and either natural bone or a femoral prosthesis component thereby producing undesirable shearing loads on the acetabular hip prosthesis causing loosening. Where, as in the alternate hip embodiment 218 illustrated in FIG. 13, the hip prosthesis 218 is kept entirely within the bony borders of the natural acetabulum, such impingement loading is avoided thereby reducing any tendency for loosening of the acetabular component due to such impingement.

It will be understood that the metal acetabular cup 220, similar to the earlier described metal acetabular cup 20, is also provided with a plurality of screw holes having recessed spherical seats for receiving metal screws (e.g. metal screw 90 of FIG. 4) to temporarily fixture the cup 220 to the hip bone (e.g. hip bone 10 of FIG. 1). Two of such screw holes are shown in FIG. 9 and identified as 266 and 268. Also, similarly, the cup 220 and plastic bearing liner 230 are provided with mutually engageable retaining means for maintaining them together upon assembly, viz. respective mating annular groove 264 and annular ridge 290 of complementary configuration as shown in FIGS. 9 and 10, as with the annular groove 64 and annular ridge 90 of FIGS. 2A and 3A, the inferior aspect of the groove 264 and ridge 290 are interrupted or relieved inferiorly by the cutting planes C'—C' of FIGS. 9 and 10 which, in particular, increases the flexibility of the ridge 290 and permits the liner 230 to be readily "snap-fitted" into the cup 220 by the application of spherically inwardly directed assembly forces generated digitally and quite easily by the fingers of the operating orthopaedic surgeon.

Figure 14B:
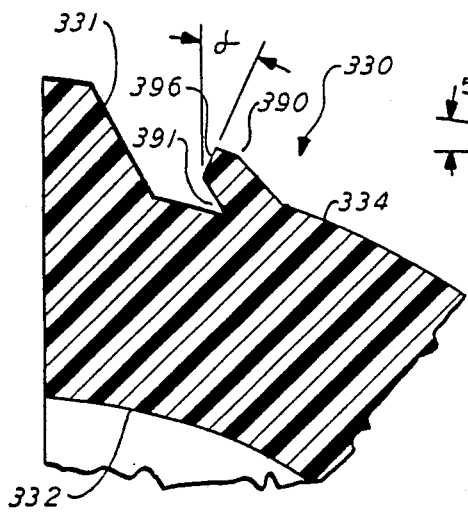
FIGS. 14A and 14B are, respectively, partial cross-sectional views of the superior aspect of the acetabular cup and plastic bearing liner of the alternate embodiment of FIGS. 8–10.

Referring now to FIGS. 14-19, there is shown a further alternate embodiment of the present invention including an alternate metal acetabular cup 320 (e.g. FIG. 14A) and an alternate plastic bearing liner 330 (e.g. FIG. 14B). For convenience of presentation, only the cross-sectional views of the upper face or rim portions of the cup 320 and liner 330 are shown because it will be understood that the cup 320 and liner 330 are each a "segmented open shell" as defined above with each having a major inferior loading bearing segment resisting assembly and disassembly forces removed to increase the flexibility of the walls of the components and facilitate their assembly and disassembly. Except for the structural differences to be described, the cup 320 otherwise may be similar to either the cup 20 (FIG. 2A) or 220 (FIG. 9) and the liner 320 otherwise may be similar to the liner 30 (FIG. 3A), liner 130 (FIG. 3B) or liner 230 (FIG. 10).

Figure 14A:
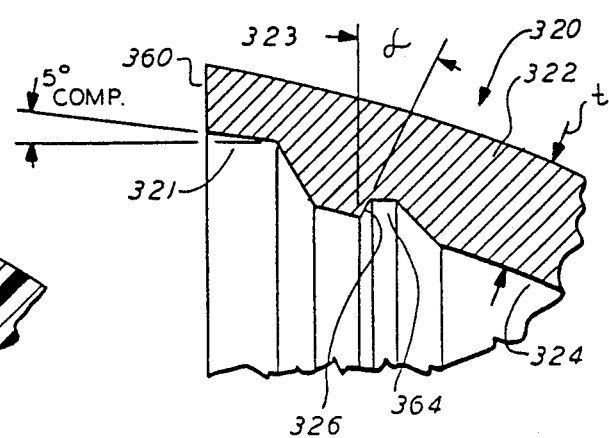
Figure 15B:
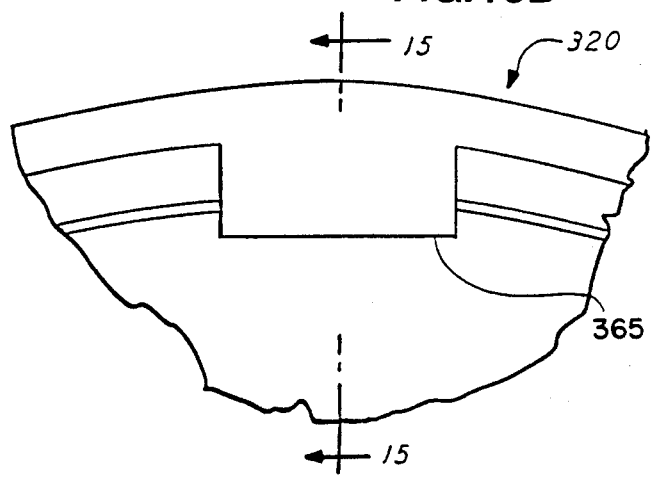
FIG. 15B is a front elevational view of the acetabular cup of the further alternate embodiment.
Figure 15A:
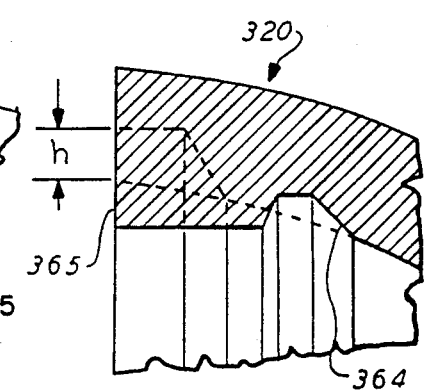
FIG. 15A is a cross-sectional view taken generally along the line 15—15 in FIG. 15B in the direction of the arrows.

As may be noted from FIG. 14A, the metal acetabular cup 320 in addition to the annular retaining groove 364 is provided with an annular recess 321 extending inwardly from the cup face 360, also, the face 326 of the retaining groove 364 is provided with a lead in angle which in the preferred embodiment is approximately 15°.

The thickness t, indicated by the opposed arrows in FIG. 14A, is determined primarily by considerations involving the thickness of the screw head (e.g. screw head 194 of FIG. 5) upon the screw head being fully recessed within its spherical seat (e.g. spherical seat 69 of FIG. 5). The use of the annular recess 321 increases the height of the key 365 (FIGS. 15A and 15B) by an amount h indicated by the opposed arrows of FIG. 15A beyond the height of the key 65 of FIG. 2. This provides a larger key which is more effective in providing axial orientation of the plastic bearing liner, e.g. plastic bearing liner 334 of FIG. 14A, relative to the metal acetabular cup 320, in providing resistance against rotation of the plastic bearing liner 334 in the metal cup 320 which upon assembly tends to roll with respect to the metal acetabular cup due to the engaging inner spherical surface 324 of the cup 320 and the outer spherical surface 334 of the plastic bearing liner 330, and in providing visual clues to the operating orthopaedic surgeon to assist in aligning the cup and liner for assembly particularly within a surgical cavity.

Figure 16B:
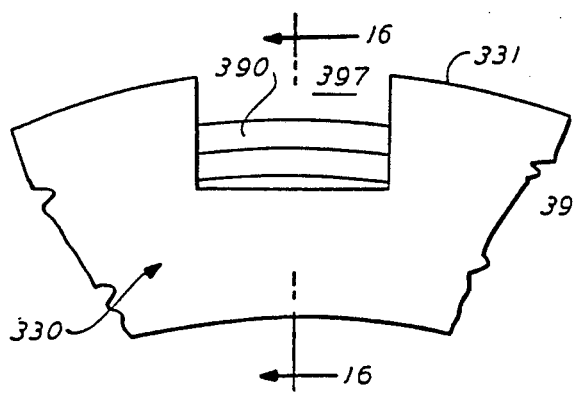
FIG. 16B is a partial front elevational view of the superior aspect of the plastic bearing liner of the further alternate embodiment of the present invention.
Figure 16A:
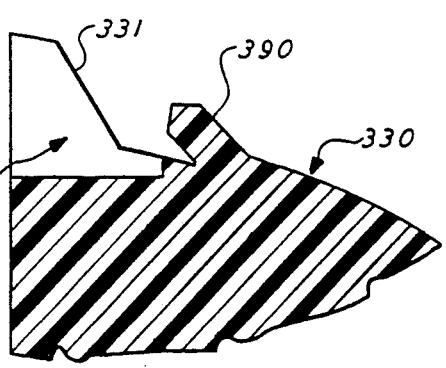
FIG. 16A is a cross-sectional view taken generally along the line 16—16 in FIG. 16B in the direction of the arrows.

The alternate embodiment plastic bearing liner 330, FIG. 14B, differs from the prior embodiments by being provided with an interrupted annular flange 331 which is complementary in shape to and which fits into the interrupted annular recess 321 (FIG. 14A) of the metal acetabular cup 320. In addition, the ridge or locking ridge 390 of FIG. 14B in this alternate embodiment differs from the prior embodiment ridge or locking ridges, e.g. ridge 90 (FIG. 3A) and ridge 290 (FIG. 10), by being provided with an undercut 391 for increasing the inward flexibility of the ridge 390 in bending. In addition, the face 396 of the locking ridge 390 is inclined at the angle α to match the lead-in angle α of the face 326 of the retaining groove 364 (FIG. 14A) formed in the metal acetabular cup 320. The plastic bearing liner 330 is provided with a keyway as shown in FIGS. 16A and 16B for receiving the key 365 (FIGS. 15A and 15B) in the same manner that the keyways receive the key in the alternate embodiments except that in this embodiment the keyway 365 and keyway are greater in height as mentioned above.

Figure 17:
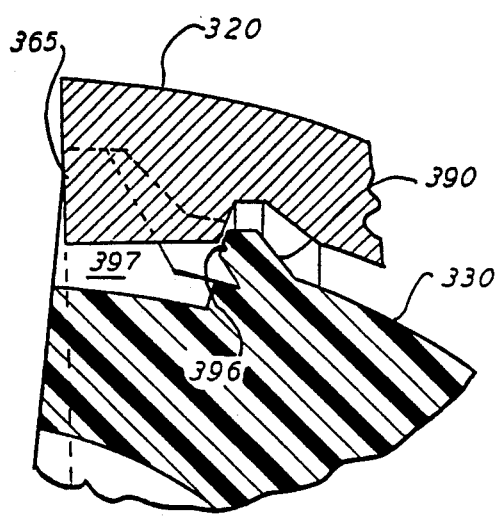
FIGS. 17-20 are sequential views showing respective stages in the assembly of the further alternate embodiment acetabular cup and plastic bearing liner.
Figure 18:
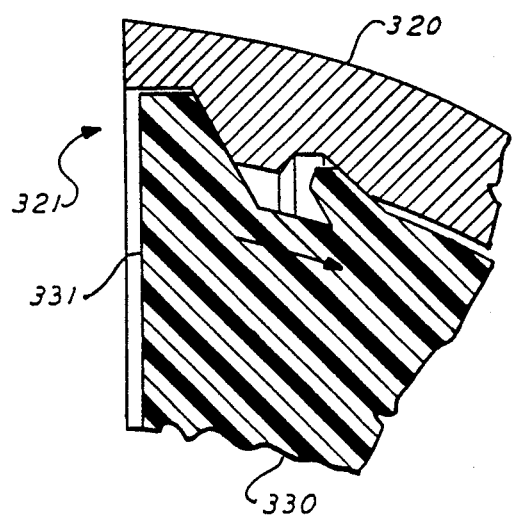
Figure 20:
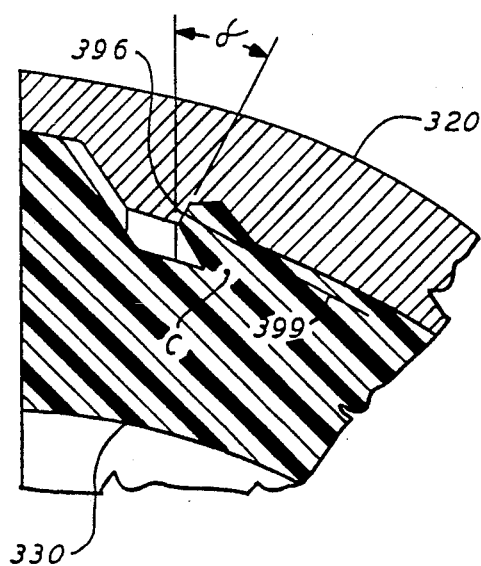

Upon assembly, FIG. 17, the superior aspect or portion of the plastic bearing liner 330 having the keyway 337 formed therein is first inserted into the metal acetabular cup 320 with the key 365 and keyway 397 aligned and with the face 396 of the locking ridge 390 engaging the back of the key 365; this partially traps the superior aspect or portion of the plastic bearing liner 330 in the metal cup 320. Now, either the anterior or posterior portion of the flange 331 of the plastic bearing liner 330 is inserted into the corresponding anterior or posterior portion of the recess 321 of the metal acetabular cup 320. This is illustrated in FIG. 18 which shows the posterior portion of the flange 331 engaging the posterior portion of the recess 321. Thus, at this point in the assembly, it will be understood that the flange 331 and recess 321 upon engagement help stabilize the plastic bearing liner 330 in the metal acetabular cup 320 against rotation in the direction of the arrows shown in FIG. 18 and prevents the above-noted rolling tendency of the spherical outer surface 334 of the liner 330 upon engaging the spherical inner surface 324 of the cup 320. At this point in the assembly, the opposite side of the plastic bearing liner insert 330, i.e. the anterior portion of the flange of the plastic bearing liner if the posterior portion is first engaged, or vice versa, is then "snap-fitted" into the recess 321 of the metal acetabular cup. This action produces deformation in the plastic bearing liner 320 which deformation takes two forms. First the anterior and posterior portions of the wall of the plastic bearing liner 330 flex inwardly due to their increased flexibility described above and secondly the locking ridge 390, which is interrupted or relieved inferiorly as described above to enhance its inward flexibility, also flexes inwardly thus facilitating assembly of the plastic bearing insert 330 with the metal acetabular cup 320; a fully assembled plastic bearing liner and metal acetabular cup are shown in FIG. 20.

Figure 19:
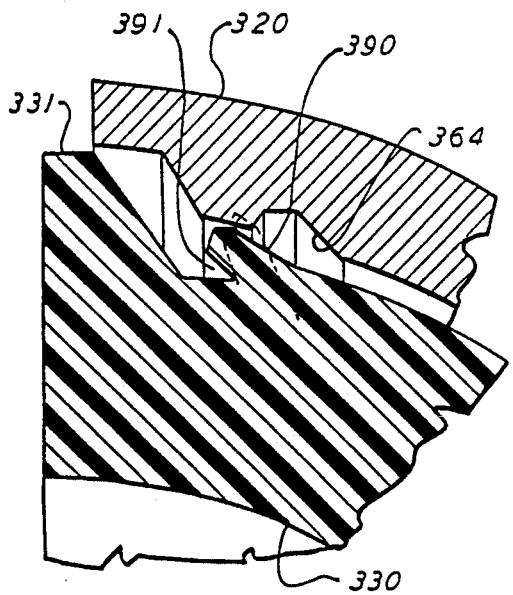

Referring to FIG. 19, the purpose of the lead-in angle α (FIGS. 14A and 14B) will now be more fully understood in that it will be understood that this angle α is needed to allow the flexible locking ridge 390 to move into the groove 364. Since the tip of the flexible locking ridge 390 first will flex or bend in the direction of the arrow of FIG. 18, the use of the matching lead-in angles α will facilitate the bending or snapping back of the flexible locking ridge 390 (in the direction opposite to the direction of the arrow (FIG. 18) and into the groove 364. It will be understood that the lead-in angle α must not be so great that the approximate location of the flexure center C (FIG. 20) of the flexible locking ridge 390 lies above a line 399 drawn perpendicular to the face 396 of the locking ridge 390.

As explained in detail above, the "segmented open shell" construction facilitates the assembly and disassembly of the acetabular cup and the plastic bearing liner by increasing the flexibility of the plastic bearing liner compared to those of nonsegmented configuration and thereby reducing the assembly and disassembly forces required. In certain situations, such as where the walls of the plastic bearing liner are thick and therefore stiff despite segmentation of the liner, it may be desirable to further facilitate the assembly and disassembly of the multi-component prosthesis. However, facilitating the assembly and disassembly of the prosthesis should not lead to a loose fit of the respective components in their assembled condition. The seemingly incompatible objective are achieved by the embodiments of the metal acetabular cup 420 and the plastic bearing liner 430 illustrated in FIGS. 21-30.

The cup 420, as shown in FIGS. 21-24, is structurally similar to the cups 20, 220 and 320 described above. In particular, the cup 420 is of segmented open shell construction with an inferior load bearing segment resisting assembly and disassembly forces removed to increase the flexibility of the walls. The cup 420 is defined by a plurality of cutting planes or surfaces to define a cup face edge 460, which is substantially similar to the cup faces 260 and 360 described in detail with respect to the cups 220 and 320 respectively.

The cup 420 includes opposed outer and inner spherical surfaces 423 and 424 respectively, and is further characterized by a plurality of screw holes 466–468 through which metal screws, such as the metal screw 90 of FIG. 4, may extend to temporarily fixture the cup 420 to the hip bone, such as the hip bone 10 shown in FIG. 1. As noted with the previously described embodiments, the screw holes 466–468 comprise recessed spherical seats 469 to enable the secure seating of the screw head at a plurality of different angles in accordance with the location of the most desirable bone stock in the patient.

Figure 21:
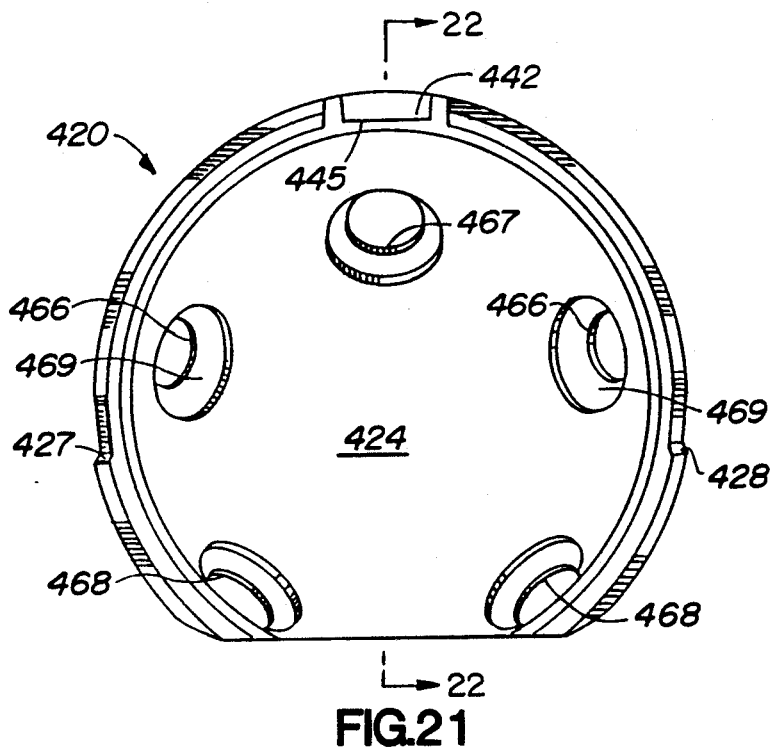
FIG. 21 is a front elevational view showing the interior of still a further embodiment of an acetabular cup in accordance with the subject matter.
Figures 22, 23:
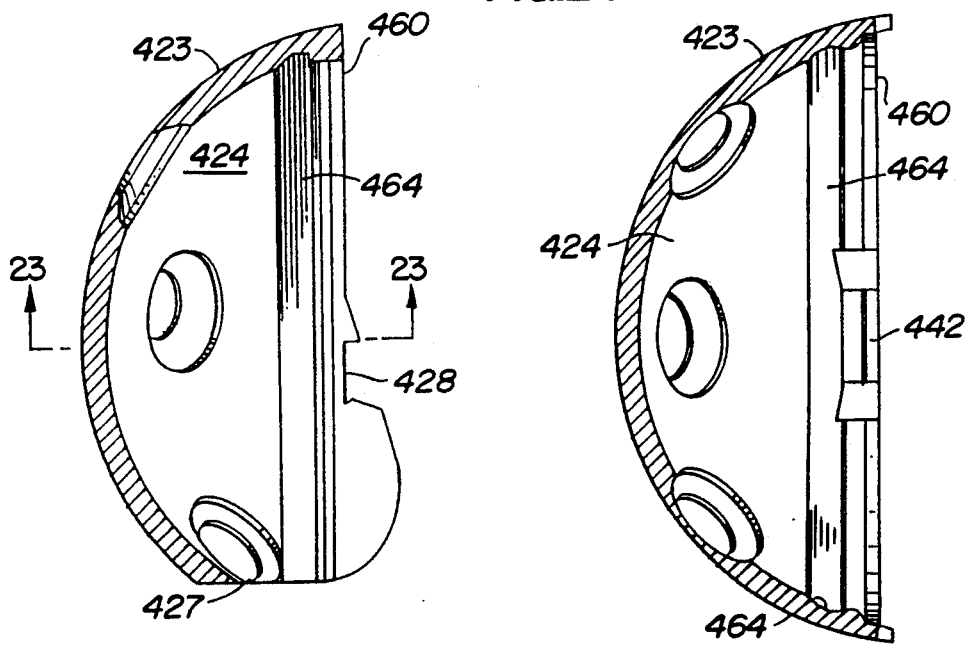
FIG. 22 is a cross-sectional view taken along line 22—22 in FIG. 21.
FIG. 23 is a cross-sectional view taken along line 23—23 in FIG. 22.
Figure 24:
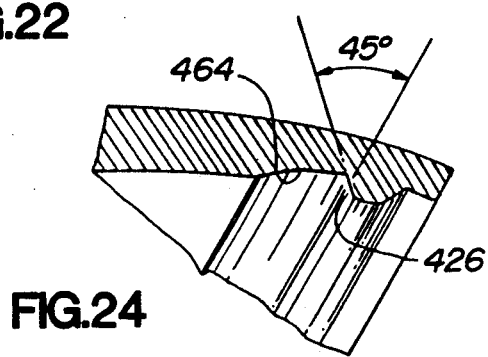
FIG. 24 is a cross-sectional view showing the peripheral ridge and groove of the acetabular cup illustrated in FIGS. 21-23.

The cup 420, as shown in FIGS. 21 and 22, includes a pair of opposed keyways 427 and 428 which are disposed for receiving complementary keys 437 and 438 on the plastic bearing liner 430 which with the key 442 in the cup and keyway 456 in the plastic bearing liner align the cup and liner and prevent relative rotation between the cup 420 and plastic bearing liner 430 in response to torsional load created during articulation of the hip joint.

As with the previously described embodiment, the cup 420 is characterized by an annular recess 421 and an annular retaining groove 464 which extend generally parallel to a planar portion of the cup face edge 460. The retaining groove 464 is defined in part by a face 426 which is aligned at a lead-in angle of approximately 45°, as shown most clearly in FIG. 24. This lead-in angle of approximately 45° is greater than the lead-in angle of approximately 15° as defined by the face 326 in the previous cup embodiment 320 depicted in FIG. 14A. The larger lead-in angle shown in FIG. 24 substantially conforms to the shape of the ridges on the plastic bearing liner 430, as explained further below to prevent relative movement between the cup 420 and the plastic bearing liner in their assembled condition.

Figure 29:
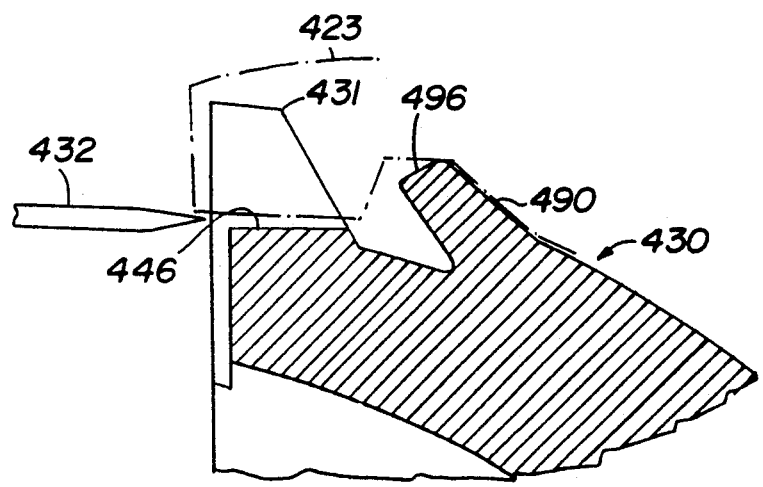
FIG. 29 is a cross-sectional view showing the ridge of the liner shown in FIGS. 25-28.
Figure 30:
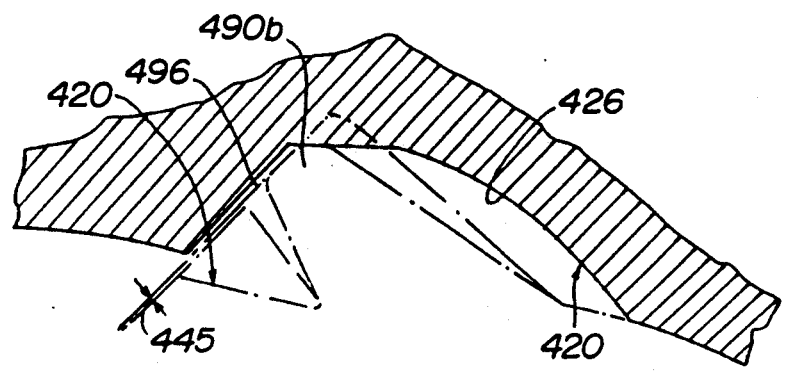
FIG. 30 is a cross-sectional view showing the ridge of the liner of FIGS. 25-29 engaged in the groove of the cup shown in FIGS. 21-24.

To disassemble the plastic bearing liner 420 from the cup 430, a sharp lever-type tool 500 can be inserted into the small gap 445 shown in FIG. 29 intermediate the inferior surface 444 of the key 442 of cup 420 and the bottom 446 of the keyway 456 of plastic bearing liner 430 to pry the plastic bearing liner 430 out of its seated position.

Figure 28:
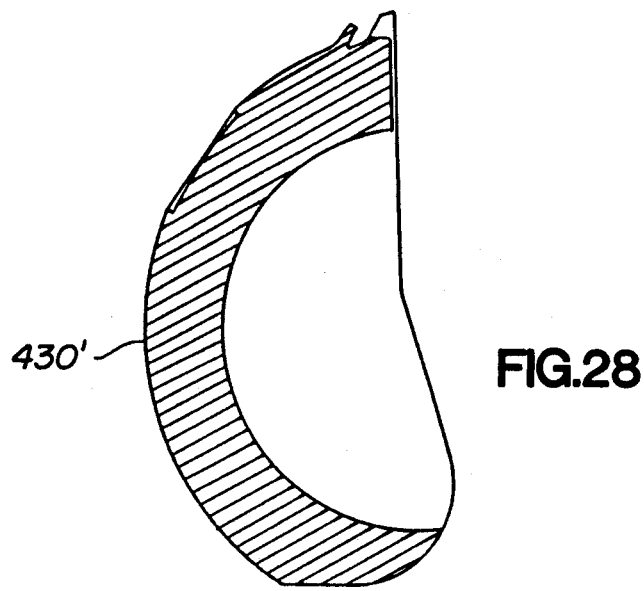
FIG. 28 is a cross-sectional view similar to FIG. 27 but showing a liner of greater radial thickness.

Turning to FIGS. 25-29, the plastic bearing liner 430 includes inner and outer spherical surfaces 432 and 434 respectively with the outer spherical surface 434 substantially conforming to the size and shape of the inner cylindrical surface 424 of the cup 420. The inner spherical surface 432 of the plastic bearing liner 430 is selected to conform to the size and shape of the spherical head on the femoral component of the prosthesis used therewith. In this regard, FIG. 27 shows a plastic bearing liner 430 for use with a femoral component having a relatively large head. FIG. 28 on the other hand shows a plastic bearing liner 430' with an outer spherical surface 434 dimensioned to mate with the inner spherical surface 424 of the cup 420, but with an inner spherical surface 432 dimensioned to mate with a femoral component having a relatively smaller radius head.

Returning to FIGS. 25 and 26, the plastic bearing liner 430 is of the same segmented open shell configuration described with respect to the cup 420 and the previously described plastic bearing liners 230 and 330. The plastic bearing liner 430 comprises an interrupted annular flange 431 which is similar to the flange 331 of the previously described embodiment and which is dimensioned to be received within the annular recess 421 of the cup 420. Similarly, the annular flange 431 is interrupted by a keyway 456 disposed to be in line with the key 442 on the cup 420 producing access to the gap 445 into which a sharp tool 500 may be inserted to separate the liner 430 from the cup 420. The annular flange 431 is further interrupted by the segmented open shell construction of the liner 430 as explained in detail above.

The liner 430 is characterized by keys 437 and 438 which are disposed and dimensioned to be received in the keyways 427 and 428 of the cup 420. As noted above, the interengagement between the keys 437, 438 and 442 and the corresponding keyways 427, 428 and 456 align the cup and liner prevent relative rotation between the liner 430 and the cup 420 in response to torsional forces created by articulation of the hip joint.

The liner 430 is further characterized by a plurality of independent resiliently deflectable locking ridges 490a, 490b and 490c extending generally around the periphery of the liner 430 and generally parallel to the interrupted annular flange 431. As shown in the broken lines of FIG. 25, the adjacent but separate locking ridges 490a-b and 490b-c may be separated from one another by a slot which permits each locking ridge 490a, 490b and 490c to deflect independently of one another. However, an alternate embodiment as shown in the solid lines provides substantial angular spacing between the adjacent locking ridges 490a, 490b and 490c. The separation between the locking ridges 490a-c enables each ridge to deflect independent of the others, reducing the forces needed to deflect each ridge and thereby greatly facilitating the bending of the locking ridges 490a-c during both assembly and disassembly of the liner 430 and the cup 420. In the particularly preferred embodiments, each locking ridge 490a-c extends through an angle of between approximately 30° and 60°, with the preferred angle being between approximately 40° and 45°. The particular angle for each locking ridge 490a-c would be selected in accordance with the relative preferred assembly and disassembly forces, which in turn would depend upon the particular materials employed for the cup 420 and liner 430 and upon the relative dimensions. The ridge construction indicated in the solid lines of FIG. 25 increases the ridge flexibility by both permitting the ridges to function independently and by reducing the total length of the ridges that must be deformed during the installation process, thereby reducing assembly forces and facilitating assembly. The same principles apply during disassembly, and thus the separate ridges 490a-c shown in FIG. 25 substantially facilitate removing the liner 430 from the cup 420.

Although the cup 420 and liner 430 depicted in FIGS. 21-30 can be easily assembled and disassembled, it is desirable to prevent relative movement therebetween. The embodiment depicted in these latter Figures achieve this objective with an interference fit obtained by providing an outside radius on the undeflected locking ridge 490a-c which exceeds the inside radius of the annular groove 464 by approximately 0.002-0.008 inch for all cups 420 and plastic bearing liners within the specified tolerances and for the smallest plastic bearing liner 430 within the specified tolerances, there will still be deflection of the ridges 490a-c in the fully seated condition of the cup 420 and plastic bearing liner 430. As a specific example, the groove 464 of the cup 420 may define an inner diameter of 1.594±0.003 inch, while the outer diameter defined by the ridges 490a-c of the plastic bearing liner 430 may be 1.604±0.004 inch. Thus, the locking ridges will be inwardly deflected by between approximately 0.1% and 0.4% of the diameter of the bearing liner upon assembly of the cup and bearing liner. Thus, as shown most clearly in FIG. 30, the ridges 490a-c are maintained in an inwardly deflected state with appropriate biasing forces being exerted against the radially outer base of groove 464 of the cup 420. This interference fit with the radially outwardly directed forces by the deflected ridges 490a-c substantially prevents relative movement between the plastic bearing liner 430 and cup 420.

Movement between the plastic bearing liner 430 and the cup 420 is further prevented by aligning the ridge end 496 at an angle of approximately 45°, or substantially equal to the angle defined by the face 426 of the cup 420. By making these angles equal at approximately 45°, a smaller clearance 445 therebetween is obtained, the ridge end 496 and the face 426 are in face-to-face contact, and there is less likelihood of movement between the components in response to forces parallel to the generating axis of the cup 420 and plastic bearing liner 430.

The plastic bearing liner 430 is assembled into the cup 420 in substantially the manner explained above. In this assembled condition, the interengagement of the keys 427, 428 and 442 in the keyways 437, 438 and 456 respectively prevents relative rotational movement of the plastic bearing liner 430 and cup 420. The deflection and snapping engagement of the independent ridges 490a-c into the groove 464 greatly facilitates this assembly of components. However, the relative radial dimensions of the ridges 490a-c and the groove 464 maintain the ridges 490a-c in a deflected condition when the plastic bearing liner 430 and cup 420 are assembled to prevent relative movement. It will be appreciated that the above described plastic bearing liner 430 and cup 420 cooperate to simultaneously achieve the seemingly dichotomous objectives of facilitating assembly and obtaining a more secure engagement. In particular, the segmentation of ridges 490a-c increases flexibility of the ridges 490a-c and therefore facilitates assembly. However, this same flexibility due to the segmentation also enables the ridges to be in a deflected condition in the groove 464 thereby achieving a secure engagement.

It will be understood by those skilled in the art, i.e. the joint prosthesis art, that the terms of reference used in the appended claims and hereinabove, viz. anterior and posterior, inferior and superior, medial and lateral, and the orientation of the acetabular components and bearing liners as shown in the drawings, except for FIG. 1, are with reference to the left natural acetabulum as viewed facing the human body, and that such terms are merely terms of reference.

Further, it will be understood by those skilled in the art that the prosthesis described above is the subject of many variations and modifications all within the scope of the present invention and that the present invention is limited only by the scope of the appended claims. For example, the above described independently deflectable segmented ridges need not be used with the segmented open shell since both structures can often achieve the same or similar objectives, and thus may be employed independently.

What is claimed is:

1. A joint prosthesis comprising first and second components dimensioned and configured to be assembled in interengaged relationship, said first and second components each define a segmented open shell, said first component comprising at least one surface and a plurality of spaced apart elongated ridges extending in generally end-to-end alignment around the surface, each said ridge being independently resiliently deflectable relative to the other of said ridges and relative to remaining portions of said first component, said second component comprising at least one groove for engagement with the spaced apart elongated ridges of the first component for retaining said first and second components in interengaged relationship, whereby the independent resilient deflectability of the ridges facilitates assembly of the first and second components.

2. A joint prosthesis as in claim 1 wherein said ridges are dimensioned to be in a deflected condition when said ridges are engaged in said groove, such that said deflected ridges exert forces against said groove for substantially preventing movement between said components.

3. A joint prosthesis as in claim 1 wherein a portion of at least one of said components comprises at least one slot to enable insertion of a tool intermediate said components to facilitate disengagement thereof.

4. A joint prosthesis comprising first and second components dimensioned and configured to be assembled in interengaged relationship, said first and second components respectively define a liner and a cup, said liner being removably engaged with said cup, said cup and said liner each defining segmented open shells defined by a plurality of non-parallel intersecting cutting surfaces, a groove being formed in said cup generally parallel to a first of said cutting surfaces thereof, said liner comprising a plurality of spaced apart elongated ridges which are independently resiliently deflectable relative to one another and relative to remaining portions of said liner, said ridges being generally arcuate and extending outwardly from said liner for engagement with the groove of said cup in the assembled condition of said joint prosthesis, whereby said arcuate ridges are independently flexible to facilitate engagement and disengagement of said liner and cup.

5. A joint prosthesis as in claim 4 wherein said ridges are disposed in generally end-to-end abutting relationship.

6. A joint prosthesis as in claim 4 wherein said ridges are angularly spaced from one another.

7. A joint prosthesis as in claim 4 wherein the outermost portion of said liner defined by said ridges in the undeflected condition thereof defines a radius which exceeds the inner radial dimension of said groove, whereby said resilient ridges are in a deflected condition when said liner is engaged in said cup, thereby exerting resilient biasing forces against said cup to substantially prevent movement therebetween.

8. A joint prosthesis as in claim 7 wherein the ridges are deflected between approximately between 0.1% and 0.5% of the liner diameter in the assembled condition of said prosthesis.

9. A joint prosthesis as in claim 4 wherein said groove is defined in part by a generally annular face angularly aligned to said first cutting surface at an angle of approximately 45°, and whereby said ridges each comprise an end face disposed substantially in face-to-face contact with said face of said groove.

10. A joint prosthesis comprising an acetabular cup and a bearing liner engaged in said cup, said cup and said liner each being substantially spherically generated and being formed to define open shells having face edges substantially surrounding the openings to said shells, said acetabular cup comprising a generally annular groove extending generally radially outwardly in said acetabular cup and generally parallel to the face edge thereof, said bearing liner comprising an outer surface and a plurality of elongated locking ridges extending less than completely around the outer surface of the spherically generated liner, each said locking ridge including a longitudinal side disposed outwardly from said outer surface of said bearing liner and engaged in the groove of said acetabular cup, said ridges being independently resiliently deflectable relative to one another and relative to said outer surface of said bearing liner, said locking ridges having a radius selected to cause said ridges to be deflected radially inwardly relative to said outer surface of said bearing liner when said bearing liner is engaged is said acetabular cup, whereby the independent resilient deflectability of the ridges facilitates assembly of the bearing liner and the acetabular cup.

11. A joint prosthesis as in claim 10 wherein the locking ridges are deflected radially inwardly by said acetabular cup by between approximately 0.1% and 0.4% of the diameter of the bearing liner.

12. A prosthesis as in claim 11 wherein said locking ridges lie substantially in a common plane, but are radially spaced from one another about the spherically generated bearing liner.

13. A joint prosthesis as in claim 12 wherein said locking ridges are in substantially end-to-end abutting relationship.

14. A joint prosthesis as in claim 10 wherein the groove of said acetabular cup includes a face aligned approximately at 45° to the first face edge of said acetabular cup, and wherein the end of said ridge is angularly aligned to be disposed in substantially face-to-face contact with the face of said groove in the assembled condition of said joint prosthesis.

15. A joint prosthesis as in claim 10 wherein said acetabular cup and said liner comprise key means for preventing relative rotational movement therebetween.

16. A joint prosthesis as in claim 10 wherein the open shells define segmented open shells such that said face edges of the cup and the liner each comprise a first face edge portion and at least one additional face edge portion angularly aligned to and intersection said first face edge portion such that a major stiffening segment of each said shell is removed to increase the flexibility of the spherically generated shell walls.

17. A joint prosthesis comprising first and second components, each said component defining a segmented open shell having a plane of symmetry, said first and second components each being defined by a first planar cutting surface substantially perpendicular to said plane of symmetry, a second planar cutting surface substantially perpendicular to said plane of symmetry and in nonparallel relationship to said first planar cutting surface, and at least one cutting surface extending between and connecting said first and second planar cutting surfaces, said second component comprising a groove formed therein and extending generally parallel to the first planar cutting surface thereof, said first component comprising a plurality of resiliently deflectable ridges extending generally parallel to the first planar cutting surface, the ridges of said first component being disposed to engage the groove of said second component for retaining said first and second components in interengaged relationship.

* * * * *